US007867159B2

(12) United States Patent
Dolecek et al.

(10) Patent No.: US 7,867,159 B2
(45) Date of Patent: *Jan. 11, 2011

(54) CENTRIFUGE SYSTEM UTILIZING DISPOSABLE COMPONENTS AND AUTOMATED PROCESSING OF BLOOD TO COLLECT PLATELET RICH PLASMA

(75) Inventors: Victor D. Dolecek, Englewood, CO (US); Gary L. Berg, Edina, MN (US); Kenneth E. Merte, Maple Grove, MN (US); David Malcolm, Parker, CO (US); Kevin D. McIntosh, Brooklyn Park, MN (US); Vitaly G. Sitko, Medina, MN (US)

(73) Assignee: Arteriocyte Medical Systems, Inc., Cleveland, OH (US)

( * ) Notice: Subject to any disclaimer, the term of this patent is extended or adjusted under 35 U.S.C. 154(b) by 197 days.

This patent is subject to a terminal disclaimer.

(21) Appl. No.: 11/810,071

(22) Filed: Jun. 4, 2007

(65) Prior Publication Data

US 2007/0293385 A1  Dec. 20, 2007

Related U.S. Application Data

(60) Division of application No. 11/271,434, filed on Nov. 10, 2005, now Pat. No. 7,252,758, which is a continuation of application No. 10/340,702, filed on Jan. 10, 2003, now Pat. No. 6,982,038.

(60) Provisional application No. 60/388,877, filed on Jun. 14, 2002.

(51) Int. Cl.
*B04B 11/00* (2006.01)
(52) U.S. Cl. .................. 494/43; 210/512.1; 494/84; 494/85

(58) Field of Classification Search ............. 494/16–18, 494/23, 27, 31, 32, 45, 85, 37, 84; 210/188, 210/511, 512.1; 422/70, 100, 104; 604/5.01, 604/6.01–6.03, 6.15, 6.16, 19, 27
See application file for complete search history.

(56) References Cited

U.S. PATENT DOCUMENTS 424,132 A   3/1890   Regensteiner et al (Continued)

FOREIGN PATENT DOCUMENTS

| DE | 27 01 976 | 7/1978 |
|---|---|---|
| EP | 0 582 257 | 8/1993 |
| EP | 1 000 664 | 5/2000 |
| WO | 96/40322 | 12/1996 |
| WO | 03/026802 | 4/2003 |

OTHER PUBLICATIONS

PCT International Search Report from International Application No. PCT/US2003/18527, dated Feb. 13, 2004.

*Primary Examiner*—Joesph W Drodge
(74) *Attorney, Agent, or Firm*—Mintz, Levin, Cohn, Ferris, Glovsky and Popeo PC

(57) ABSTRACT

A centrifugal method, and corresponding system, for processing blood to collect platelet rich plasma. A separation chamber is filled with blood from a fill syringe by rotating the separation chamber at a fill rotation rate and pumping the blood from the fill syringe. A soft spin is used to initially separate red blood cells from platelets by spinning the separation chamber at a soft spin rate. A percentage of the blood is drawn from the separation chamber back into the fill syringe to remove separated red blood cells. A second portion of the separated blood is drawn from the separation chamber until a red blood cell/platelet interface is detected. A hard spin is performed by spinning the separation chamber at a higher rate and connecting tubing is cleared of red blood cells by drawing a predetermined clearing volume. The platelet rich plasma is then collected in the collection syringe.

5 Claims, 16 Drawing Sheets

U.S. PATENT DOCUMENTS

| | | |
|---|---|---|
| 3,655,123 A | 4/1972 | Judson et al. |
| 3,724,747 A | 4/1973 | Unger et al. |
| 3,737,096 A | 6/1973 | Jones et al. ............... 233/19 A |
| 3,987,961 A | 10/1976 | Sinn et al. |
| 4,010,894 A | 3/1977 | Kellogg et al. |
| 4,098,456 A * | 7/1978 | Bayham ...................... 494/17 |
| RE29,738 E | 8/1978 | Adams ...................... 350/6.5 |
| 4,113,173 A * | 9/1978 | Lolachi ...................... 494/18 |
| 4,146,172 A | 3/1979 | Cullis et al. |
| 4,185,629 A | 1/1980 | Cullis et al. |
| 4,194,684 A * | 3/1980 | Boggs ........................ 494/18 |
| 4,215,688 A | 8/1980 | Terman et al. |
| 4,268,393 A | 5/1981 | Persidsky et al. |
| 4,303,193 A | 12/1981 | Latham, Jr. ............... 233/23 A |
| 4,303,336 A | 12/1981 | Cullis |
| 4,322,298 A | 3/1982 | Persidsky |
| 4,350,283 A | 9/1982 | Leonian ...................... 233/26 |
| 4,402,680 A | 9/1983 | Schoendorfer |
| 4,409,106 A | 10/1983 | Furuta et al. |
| 4,421,503 A | 12/1983 | Latham, Jr. et al. |
| 4,439,178 A * | 3/1984 | Mulzet ....................... 494/85 |
| 4,445,883 A | 5/1984 | Schroendorfer |
| 4,530,691 A | 7/1985 | Brown |
| 4,637,813 A | 1/1987 | DeVries |
| 4,648,863 A | 3/1987 | Nees |
| 4,680,025 A | 7/1987 | Kruger et al. |
| 4,720,284 A | 1/1988 | McCarty |
| 4,828,716 A * | 5/1989 | McEwen et al. ............ 210/740 |
| 4,834,890 A | 5/1989 | Brown et al. |
| 4,871,462 A | 10/1989 | Fischel et al. |
| 4,889,524 A | 12/1989 | Fell et al. ...................... 494/12 |
| 4,939,087 A | 7/1990 | Van Wie et al. ........ 435/240.25 |
| 4,944,883 A | 7/1990 | Schoendorfer et al. |
| 4,985,153 A | 1/1991 | Kuroda et al. |
| 4,997,577 A | 3/1991 | Stewart |
| 5,076,911 A | 12/1991 | Brown et al. |
| 5,100,372 A | 3/1992 | Headley |
| 5,104,526 A | 4/1992 | Brown et al. |
| 5,128,048 A | 7/1992 | Stewart et al. |
| 5,147,290 A | 9/1992 | Jonsson |
| 5,152,905 A | 10/1992 | Pall et al. |
| 5,180,504 A | 1/1993 | Johnson et al. |
| 5,184,188 A | 2/1993 | Bull et al. |
| 5,217,627 A | 6/1993 | Pall et al. |
| 5,224,921 A | 7/1993 | Dennehey et al. |
| 5,234,608 A | 8/1993 | Duff |
| 5,269,946 A | 12/1993 | Goldhaber et al. |
| 5,316,540 A | 5/1994 | McMannis et al. ............ 494/37 |
| 5,316,666 A | 5/1994 | Brown et al. |
| 5,316,667 A | 5/1994 | Brown |
| 5,322,620 A | 6/1994 | Brown et al. |
| 5,370,802 A | 12/1994 | Brown |
| 5,403,272 A | 4/1995 | Deniega et al. |
| 5,437,598 A | 8/1995 | Antwiler |
| 5,494,578 A | 2/1996 | Brown et al. |
| 5,496,265 A | 3/1996 | Langley et al. |
| 5,505,685 A | 4/1996 | Antwiler |
| 5,512,187 A | 4/1996 | Buchholz et al. |
| 5,514,069 A | 5/1996 | Brown et al. |
| 5,525,218 A * | 6/1996 | Williamson et al. ......... 210/232 |
| 5,527,472 A | 6/1996 | Bellotti et al. |
| 5,529,691 A | 6/1996 | Brown |
| 5,543,060 A | 8/1996 | Pall et al. |
| 5,547,453 A | 8/1996 | Di Perna |
| 5,547,591 A | 8/1996 | Hagihara et al. |
| 5,551,942 A | 9/1996 | Brown et al. |
| 5,573,678 A | 11/1996 | Brown et al. |
| 5,580,465 A | 12/1996 | Pall et al. |
| 5,585,007 A | 12/1996 | Antanavich et al. |
| 5,587,070 A | 12/1996 | Pall et al. |
| 5,601,727 A | 2/1997 | Bormann et al. |
| 5,614,106 A | 3/1997 | Payrat et al. |
| 5,616,254 A | 4/1997 | Pall et al. |
| 5,628,915 A | 5/1997 | Brown et al. |
| 5,632,893 A | 5/1997 | Brown et al. |
| 5,641,414 A | 6/1997 | Brown |
| 5,649,903 A | 7/1997 | Deniega et al. |
| 5,651,766 A | 7/1997 | Kingsley et al. |
| 5,653,887 A | 8/1997 | Wahl et al. |
| 5,656,154 A | 8/1997 | Meryman |
| 5,656,163 A | 8/1997 | Brown |
| 5,658,240 A | 8/1997 | Urdahl et al. |
| 5,674,173 A | 10/1997 | Hlavinka et al. |
| 5,676,644 A | 10/1997 | Toavs et al. |
| 5,681,273 A | 10/1997 | Brown |
| 5,690,602 A | 11/1997 | Brown et al. |
| 5,690,815 A | 11/1997 | Krasnoff et al. |
| 5,690,835 A | 11/1997 | Brown |
| 5,693,232 A | 12/1997 | Brown et al. |
| 5,702,357 A | 12/1997 | Bainbridge et al. |
| 5,702,383 A | 12/1997 | Giesler et al. |
| 5,704,889 A | 1/1998 | Hlavinka et al. |
| 5,712,798 A | 1/1998 | Langley et al. |
| 5,720,716 A | 2/1998 | Blakeslee et al. |
| 5,722,926 A | 3/1998 | Hlavinka et al. |
| 5,722,946 A | 3/1998 | Mudloff et al. |
| 5,723,050 A | 3/1998 | Unger et al. |
| 5,728,060 A | 3/1998 | Kingsley et al. |
| 5,738,644 A | 4/1998 | Holmes et al. |
| 5,738,784 A | 4/1998 | Holm et al. |
| 5,750,025 A | 5/1998 | Holmes et al. |
| 5,770,069 A | 6/1998 | Meryman |
| 5,779,660 A | 7/1998 | Kingsley et al. |
| 5,788,662 A | 8/1998 | Antanavich et al. |
| 5,792,038 A | 8/1998 | Hlavinka |
| 5,792,372 A | 8/1998 | Brown et al. |
| 5,795,317 A | 8/1998 | Brierton et al. |
| 5,807,492 A | 9/1998 | Brown et al. |
| 5,824,230 A | 10/1998 | Holm et al. |
| 5,836,734 A | 11/1998 | Doering |
| 5,837,150 A | 11/1998 | Langley et al. |
| 5,853,382 A | 12/1998 | Kingsley et al. |
| 5,865,785 A | 2/1999 | Bischof |
| 5,876,321 A | 3/1999 | Hlavinka et al. |
| 5,913,768 A | 6/1999 | Langley et al. |
| 5,919,154 A | 7/1999 | Toavs et al. |
| 5,921,950 A | 7/1999 | Toavs et al. |
| 5,939,319 A | 8/1999 | Hlavinka et al. |
| 5,941,842 A | 8/1999 | Steele et al. |
| 5,951,877 A | 9/1999 | Langley et al. |
| 5,954,626 A | 9/1999 | Hlavinka |
| 5,956,023 A | 9/1999 | Lyle et al. |
| 5,958,250 A | 9/1999 | Brown et al. |
| 5,961,842 A | 10/1999 | Min et al. |
| 5,964,724 A | 10/1999 | Rivera et al. |
| 5,970,423 A | 10/1999 | Langley et al. |
| 5,980,760 A | 11/1999 | Min et al. |
| 5,993,370 A | 11/1999 | Brown et al. |
| 6,007,509 A | 12/1999 | Kingsley et al. |
| 6,010,627 A | 1/2000 | Hood, III |
| 6,022,306 A | 2/2000 | Dumont et al. |
| 6,051,146 A | 4/2000 | Green et al. |
| 6,051,147 A | 4/2000 | Bischof |
| 6,059,979 A | 5/2000 | Brown |
| 6,071,422 A | 6/2000 | Hlavinka et al. |
| 6,102,883 A | 8/2000 | Kingsley et al. |
| 6,106,727 A | 8/2000 | Krasnoff et al. |
| 6,129,656 A | 10/2000 | Blakeslee et al. |
| 6,143,247 A | 11/2000 | Sheppard et al. |
| 6,168,561 B1 | 1/2001 | Cantu et al. |
| 6,179,801 B1 | 1/2001 | Holmes et al. |
| 6,183,651 B1 | 2/2001 | Brown et al. |
| 6,196,987 B1 | 3/2001 | Holmes et al. |
| 6,200,287 B1 | 3/2001 | Keller et al. |

| | | | | | |
|---|---|---|---|---|---|
| 6,228,017 B1 | 5/2001 | Brown | 6,596,180 B2 | 7/2003 | Baugh et al. .................. 210/782 |
| 6,231,537 B1 | 5/2001 | Holmes et al. | 6,596,181 B2 | 7/2003 | Dolecek et al. ............. 210/787 |
| 6,233,525 B1 | 5/2001 | Langley et al. | 6,605,028 B2 | 8/2003 | Dolecek ....................... 494/13 |
| 6,234,989 B1 | 5/2001 | Brierton et al. | 6,609,413 B1 | 8/2003 | De Craecker |
| 6,254,784 B1 | 7/2001 | Nayak et al. | 6,610,002 B2 | 8/2003 | Dolecek ....................... 494/37 |
| 6,261,065 B1 | 7/2001 | Nayak et al. | 6,612,975 B2 | 9/2003 | Malcom et al. ............... 494/84 |
| 6,261,217 B1 | 7/2001 | Unger et al. | 6,719,901 B2 | 4/2004 | Dolecek et al. |
| 6,277,060 B1 | 8/2001 | Neumann | 6,790,371 B2 | 9/2004 | Dolecek et al. ............. 210/787 |
| 6,280,622 B1 | 8/2001 | Goodrich et al. | 6,835,316 B2 | 12/2004 | Dolecek ..................... 210/787 |
| 6,284,142 B1 | 9/2001 | Muller | 6,890,728 B2 | 5/2005 | Dolecek et al. ............. 435/40.5 |
| 6,294,094 B1 | 9/2001 | Muller et al. | 6,942,639 B2 | 9/2005 | Baugh et al. .................. 604/82 |
| 6,296,602 B1 | 10/2001 | Headley | 6,942,880 B1 | 9/2005 | Dolecek ..................... 424/532 |
| 6,579,219 B2 | 6/2003 | Dolecek et al. ............... 494/37 | 6,982,038 B2 * | 1/2006 | Dolecek et al. ............. 210/739 |
| 6,582,350 B2 | 6/2003 | Dolecek ....................... 494/37 | 2002/0022213 A1 | 2/2002 | Dolecek et al. |
| 6,589,153 B2 | 7/2003 | Dolecek et al. | 2002/0144939 A1 | 10/2002 | Dolecek ..................... 210/145 |
| 6,589,155 B2 | 7/2003 | Dolecek et al. ............... 494/84 | | | |

* cited by examiner

CENTRIFUGE SYSTEM UTILIZING DISPOSABLE COMPONENTS AND AUTOMATED PROCESSING OF BLOOD TO COLLECT PLATELET RICH PLASMA

CROSS-REFERENCE TO RELATED APPLICATION

This application is a divisional application of U.S. patent application Ser. No. 11/271,434, filed Nov. 10, 2005, now U.S. Pat. No. 7,252,758, which in turn is a continuation application of U.S. patent application Ser. No. 10/340,702, filed Jan. 10, 2003, now U.S. Pat. No. 6,982,038, which claims the benefit of U.S. Provisional Application No. 60/388,877, filed Jun. 14, 2002, all of which are herein incorporated by reference in their entirety.

BACKGROUND OF THE INVENTION

1. Field of the Invention

This invention relates to novel methods and systems for the centrifugal separation of a liquid into its components of varying specific gravities and collection of these components, and more particularly, to a separation system and method for separating blood into its components and collecting platelet rich plasma and other blood components using disposable separation containers, input and output tubing, and source and collection syringes and using automated operation of system components (such as a centrifuge, syringe pumps, and valves) to separate a volume of blood in a disposable separation container into its components and then collect user-selected volumes and components (such as platelet rich plasma) from the container.

2. Relevant Background

Centrifugation utilizes the principle that particles suspended in solution will assume a particular radial position within the centrifuge rotor based upon their respective densities and will therefore separate when the centrifuge is rotated at an appropriate angular velocity for an appropriate period of time. Centrifugal liquid processing systems have found applications in a wide variety of fields. For example, centrifugation is widely used in blood separation techniques to separate blood into its component parts, that is, red blood cells, platelets, white blood cells, and plasma.

The liquid portion of the blood, referred to as plasma, is a protein-salt solution in which red and white blood cells and platelets are suspended. Plasma, which is 90 percent water, constitutes about 55 percent of the total blood volume. Plasma contains albumin (the chief protein constituent), fibrinogen (responsible, in part, for the clotting of blood), globulins (including antibodies) and other clotting proteins. Plasma serves a variety of functions, from maintaining a satisfactory blood pressure and providing volume to supplying critical proteins for blood clotting and immunity. Plasma is obtained by separating the liquid portion of blood from the cells suspended therein.

Red blood cells (erythrocytes) are perhaps the most recognizable component of whole blood. Red blood cells contain hemoglobin, a complex iron-containing protein that carries oxygen throughout the body while giving blood its red color. The percentage of blood volume composed of red blood cells is called the "hematocrit." White blood cells (leukocytes) are responsible for protecting the body from invasion by foreign substances such as bacteria, fungi and viruses. Several types of white blood cells exist for this purpose, such as granulocytes and macrophages which protect against infection by surrounding and destroying invading bacteria and viruses, and lymphocytes which aid in the immune defense. Platelets (thrombocytes) are very small cellular components of blood that help the clotting process by sticking to the lining of blood vessels. Platelets are vital to life, because they help prevent both massive blood loss resulting from trauma and blood vessel leakage that would otherwise occur in the course of normal, day-to-day activity.

If whole blood is collected and prevented from clotting by the addition of an appropriate anticoagulant, it can be centrifuged into its component parts. Centrifugation will result in the red blood cells, which weigh the most, packing to the most outer portion of the rotating container, while plasma, being the least dense will settle in the central portion of the rotating container. Separating the plasma and red blood cells is a thin white or grayish layer called the buffy coat. The buffy coat layer consists of the white blood cells and platelets, which together make up about 1 percent of the total blood volume. These blood components, discussed above, may be isolated and utilized in a wide range of diagnostic and therapeutic regimens. Various techniques and apparatus have been developed to facilitate the separation and collection of blood components. The most widely used systems are centrifugal systems, also referred to as blood-processing systems, and are usually discontinuous-flow or continuous-flow devices.

In discontinuous-flow systems, whole blood from the donor or patient flows through a conduit into the rotor or bowl where component separation takes place. These systems employ a bowl-type rotor with a relatively large (typically 200 ml or more) volume that must be filled with blood before any of the desired components can be harvested. When the bowl is full, the drawing of fresh blood is stopped, the whole blood is separated into its components by centrifugation, and the unwanted components are returned to the donor or patient through the same conduit intermittently, in batches, rather than on a continuous basis. When the return has been completed, whole blood is again drawn from the donor or patient, and a second cycle begins. This process continues until the required amount of the desired component has been collected. Discontinuous-flow systems have the advantage that the rotors are relatively small in diameter but may have the disadvantage of a relatively large extracorporeal volume (i.e., the amount of blood that is out of the donor at any given time during the process). Discontinuous-flow devices are used for the collection of platelets and/or plasma and for the concentration and washing of red blood cells. They are used to reconstitute previously frozen red blood cells and to salvage red blood cells lost intraoperatively. Because the bowls in these systems are rigid and have a fixed volume, however, it has been difficult to control the hematocrit of the final product, particularly if the amount of blood salvaged is insufficient to fill the bowl with red blood cells.

One example of a discontinuous-flow system is disclosed by McMannis, et al., in his U.S. Pat. No. 5,316,540, and is a variable volume centrifuge for separating components of a fluid medium, comprising a centrifuge that is divided into upper and lower chambers by a flexible membrane, and a flexible processing container bag positioned in the upper chamber of the centrifuge. The McMannis, et al., system varies the volume of the upper chamber by pumping a hydraulic fluid into the lower chamber, which in turn raises the membrane and squeezes the desired component out of the centrifuge. The McMannis, et al., system takes up a fairly large amount of space, and its flexible pancake-shaped rotor is awkward to handle. The McMannis, et al., system does not permit the fluid medium to flow into and out of the processing bag at the same time, nor does it permit fluid medium to be pulled out of the processing bag by suction.

In continuous-flow systems, whole blood from the donor or patient also flows through one conduit into the spinning rotor where the components are separated. The component of interest is collected and the unwanted components are returned to the donor through a second conduit on a continuous basis as more whole blood is being drawn. Because the rate of drawing and the rate of return are substantially the same, the extracorporeal volume, or the amount of blood that is out of the donor or patient at any given time in the procedure, is relatively small. These systems typically employ a belt-type rotor, which has a relatively large diameter but a relatively small (typically 100 ml or less) processing volume. Although continuous-flow systems have the advantage that the amount of blood that must be outside the donor or patient can be relatively small, they have the disadvantage that the diameter of the rotor is large. These systems are, as a consequence, large and often, are complicated to set up and use. These devices are used almost exclusively for the collection of platelets.

Continuous-flow systems are comprised of rotatable and stationary parts that are in fluid communication. Consequently, continuous-flow systems utilize either rotary seals or a J-loop. In many continuous-flow systems, rotary seals are formed by a stationary rigid low friction member contacting a moving rigid member to create a dynamic seal, and an elastomeric member that provides a resilient static seal as well as a modest closing force between the surfaces of the dynamic seal. In other systems, a pair of seal elements is provided having confronting annular fluid-tight sealing surfaces of non-corrodible material. These are maintained in a rotatable but fluid-tight relationship by axial compression of a length of elastic tubing forming one of the fluid connections to these seal elements.

One drawback present in the above-described continuous-flow systems has been their use of a rotating seal or coupling element between that portion of the system carried by the centrifuge rotor and that portion of the system that remains stationary. While such rotating seals have provided generally satisfactory performance, they have been expensive to manufacture and have added to the cost of the flow systems. Furthermore, such rotating seals introduce an additional component into the system which if defective can cause contamination of the blood being processed.

One flow system heretofore contemplated to overcome the problem of the rotating seal utilizes a rotating carriage on which a single housing is rotatably mounted. An umbilical cable extending to the housing from a stationary point imparts planetary motion to the housing and thus prevents the cable from twisting. To promote sterile processing while avoiding the disadvantages of a discontinuous-flow system within a single sealed system, a family of dual member centrifuges can be used to effect cell separation. One example of this type of centrifuge is disclosed in U.S. Pat. No. RE 29,738 to Adams entitled "Apparatus for Providing Energy Communication Between a Moving and a Stationary Terminal." Due to the characteristics of such dual member centrifuges, it is possible to rotate a container containing a fluid, such as a unit of donated blood and to withdraw a separated fluid component, such as plasma, into a stationary container, outside of the centrifuge without using rotating seals. Such container systems utilize a J-loop and can be formed as closed, sterile transfer sets.

The Adams patent discloses a centrifuge having an outer rotatable member and an inner rotatable member. The inner member is positioned within and rotatably supported by the outer member. The outer member rotates at one rotational velocity, usually called "one omega," and the inner rotatable member rotates at twice the rotational velocity of the outer housing or "two omega." There is thus a one-omega difference in rotational speed of the two members. The dual member centrifuge of the Adams patent is particularly advantageous in that, as noted above, no seals are needed between the container of fluid being rotated and the non-moving component collection containers. The system of the Adams patent provides a way to process blood into components in a single, sealed, sterile system wherein whole blood from a donor can be infused into the centrifuge while the two members of the centrifuge are being rotated. However, the Adams system and the other continuous-flow systems are generally large and expensive units that are not intended to be portable. Further, they are also an order of magnitude more expensive than a standard, multi-container blood collection set.

Whole blood that is to be separated into its components is commonly collected into a flexible plastic donor bag, and the blood is centrifuged to separate it into its components through a batch process. This is done by spinning the blood bag for a period of about 10 minutes in a large refrigerated centrifuge. The main blood constituents, i.e., red blood cells, platelets and white cells, and plasma, having sedimented and formed distinct layers, are then expressed sequentially by a manual extractor in multiple satellite bags attached to the primary bag.

More recently, automated extractors have been introduced in order to facilitate the manipulation. Nevertheless, the whole process remains laborious and requires the separation to occur within a certain time frame to guarantee the quality of the blood components. This complicates the logistics, especially considering that most blood donations are performed in decentralized locations where no batch processing capabilities exist. This method has been practiced since the widespread use of the disposable plastic bags for collecting blood in the 1970's and has not evolved significantly since then. Some attempts have been made to apply haemapheresis technology in whole blood donation. This technique consists of drawing and extracting on-line one or more blood components while a donation is performed, and returning the remaining constituents to the donor. However, the complexity and costs of haemapheresis systems preclude their use by transfusion centers for routine whole blood collection.

There have been various proposals for portable, disposable, centrifugal apparatus, usually with collapsible bags, for example as in U.S. Pat. Nos. 3,737,096, or 4,303,193 to Latham, Jr., or with a rigid walled bowl as in U.S. Pat. No. 4,889,524 to Fell, et al. These devices all have a minimum fixed holding volume which requires a minimum volume usually of about 250 ml to be processed before any components can be collected. U.S. Pat. No. 5,316,540 to McMannis, et al., discloses a centrifugal processing apparatus, wherein the processing chamber is a flexible processing bag which can be deformed to fill it with biological fluid or empty it by means of a membrane which forms part of the drive unit. The bag comprises a single inlet/outlet tubing for the introduction and removal of fluids to the bag, and consequently cannot be used in a continual, on-line process. Moreover, the processing bag has a the disadvantage of having 650 milliliter capacity, which makes the McMannis, et al., device difficult to use as a blood processing device.

Hence, there remains a need for a centrifugal system for processing blood and other biological fluids that is compact and easy to use and that does not have the disadvantages of prior-art discontinuous and/or continuous flow systems. Such a system preferably would automatically separate the different components of whole blood that are differentiable in density and size, with a simple, low cost, disposable unit without the use of rotational coupling elements. Additionally, the system would be essentially self-contained and relatively inexpensive with the blood contacting set being disposable each time the whole blood has been separated.

Reference is made to the following commonly owned patent applications which are incorporated by reference herein in their entirety: U.S. patent application Ser. No. 10/116,729, filed Apr. 4, 2002 and now U.S. Pat. No. 6,890,728, which is entitled "Methods of Isolating Blood Components Using a Centrifuge and Uses Thereof;" U.S. patent application Ser. No. 09/961,793, filed Sep. 24, 2001 and now U.S. Pat. No. 6,589,153, which is entitled "Blood Centrifuge with Exterior Mounted Self-Balancing Collection Chamber;" U.S. patent application Ser. No. 09/832,711, filed Apr. 9, 2001 and now U.S. Pat. No. 6,579,219, which is entitled "Centrifuge Bag and Methods of Use;" U.S. patent application Ser. No. 09/833,230, filed Apr. 9, 2001 and now U.S. Pat. No. 6,610,002, which is entitled "Method for Handling Blood Sample to Ensure Blood Components are Isolated;" U.S. patent application Ser. No. 09/833,231, filed Apr. 9, 2001 and now U.S. Pat. No. 6,582,350, which is entitled "Centrifuge Container having Curved Linear Shape:" U.S. patent application Ser. No. 09/832,729, filed Apr. 9, 2001 and now U.S. Pat. No. 6,942,639, which is entitled "Autologous Platelet Gel Delivery System;" U.S. patent application Ser. No. 09/832,730, filed Apr. 9, 2001 and now U.S. Pat. No. 6,612,975, which is entitled "Blood Centrifuge with an Enhanced Internal Drive Assembly;" U.S. patent application Ser. No. 09/833,232, filed Apr. 9, 2001 and now U.S. Pat. No. 6,589,155, which is entitled "Miniaturized Blood Centrifuge having Side Mounted Motor with Belt Drive;" U.S. patent application Ser. No. 09/832,881, filed Apr. 9, 2001 and now abandoned; U.S. patent application Ser. No. 09/832,741, filed Apr. 9, 2001 and now U.S. Pat. No. 6,596,181, which is entitled "Hard Shell Disposable Reservoir having Complex Internal Design for use in a Centrifuge;" U.S. patent application Ser. No. 09/832,516, filed Apr. 9, 2001 and now U.S. Pat. No. 6,605,028, which is entitled "Blood Centrifuge having Integral Heating to Control Cellular Component Temperature;" U.S. patent application Ser. No. 09/832,463, filed Apr. 9, 2001 and now U.S. Pat. No. 6,790,371, which is entitled "System and Method for Automated Separation of Blood Components;" U.S. patent application Ser. No. 09/833,233, filed Apr. 9, 2001 and now U.S. Pat. No. 6,835,316, which is entitled "Clam Shell Blood Reservoir Holder with Index Line;" U.S. patent application Ser. No. 09/833,234, filed Apr. 9, 2001 and now U.S. Pat. No. 6,596,180, which is entitled "System and Method for the Production of Autologous Platelet Gel;" U.S. patent application Ser. No. 09/832,518, filed Apr. 9, 2001 and now U.S. Pat. No. 6,942,880, which is entitled "Autologous Platelet Gel having Beneficial Geometric Shapes and Methods of Making the Same;" and U.S. patent application Ser. No. 09/832,517, filed Apr. 9, 2001 and now U.S. Pat. No. 6,719,901, which is entitled "System for the Production of Autologous Platelet Gel Useful for the Delivery of Medicinal and Genetic Agents."

SUMMARY OF THE INVENTION

The present invention addresses the above problems by providing a centrifugal method for processing blood (or other fluids) in an automated manner with ongoing self-balancing of fluids and allowing collection of user-input volumes of platelet rich plasma (PRP) (or another component if a fluid other than blood is processed). The method includes receiving a fill syringe having a volume of blood and receiving a collection syringe for use in collecting the PRP. The method continues with filling a separation chamber with the blood in the fill syringe. The filling involves rotating the separation chamber with a centrifuge at a fill rotation rate and pumping the blood from the fill syringe (such as by using a syringe pump to operate the fill syringe) through runs of tubing connecting the fill syringe and the separation chamber. A soft spin is used to initially separate the denser red blood cells from the platelets and involves operating the centrifuge to spin the separation chamber at a soft spin rotation rate higher than the fill rotation rate. A portion of the volume of the now separated blood (such as about 25 percent of the fill volume) is then drawn from the separation chamber back into the fill syringe. Typically, the centrifuge is first slowed to spin the separation chamber at a dwell rotation rate (similar to the fill rotation rate). A second portion of the separated blood is drawn from the separation chamber until a RBC/PRP interface is detected in the separation chamber. A hard spin is then performed by spinning the separation chamber at a rate higher than the soft spin rotation rate and the line and a portion of the separation chamber are cleared of RBC by drawing a line clearing volume into the fill syringe. The fill syringe is isolated (such as with a pinch valve) and a volume of the PRP is collected by operating the collection syringe with a syringe pump. The PRP volume collected can be a default value or can be a volume received from an operator via a user interface. The method may include collecting the remaining fluid from the separation chamber, i.e., collecting any remaining PRP and the platelet poor plasma (PPP).

In one aspect of the invention, a centrifuge is provided with automation features for safe and convenient separation of blood components. An automated pinch valve can be used in combination with an automated syringe loading and unloading apparatus in order to introduce and withdraw blood and blood components at designated points in the process. An automated centrifuge door latch can be used to prevent the centrifuge door from being opened at improper points in the process and to indicate to the operator that the centrifuge door is closed before the centrifuge is placed into operation.

In another aspect of the invention, a centrifuge is provided in which a skid plate provides a surface against which tubing extending from the centrifuge can be prevented from twisting, binding and failing during operation of the centrifuge. The tubing rides on the skid plate as the centrifuge spins in order to keep the shape of the tubing and frictional engagement with the centrifuge such that fluid can move through the tubing into and out of a separation chamber carried by the centrifuge without building up excess heat or affecting the function of the tubing during the separation process. Also, the tubing is preferably lubricated at the points of contact with the separation chamber, the skid plate and other rotating or rubbing components to prevent frictional heating which can cause the tubing to stretch or deform during centrifuge operation.

In another aspect of the invention, a separation chamber assembly is provided with a tubing clamp that is used to hold a portion of the tubing on an arm centered in a stationary position over the spinning centrifuge. The tubing clamp is preferably adapted to mate with the tubing such that the tubing is slightly compressed and reduced in diameter so as to be prevented from axial or rotational movement as the centrifuge is spinning. The tubing clamp is inserted into a portion of an arm that securely clamps and holds the tubing at a point that is centered at a predetermined height above the spinning centrifuge. The tubing clamp is positioned to provide a correct predetermined length of tubing between the centrifuge and the arm.

In another aspect of the invention, a compact centrifuge is provided that includes both a single-sided drive belt and a double-sided drive belt driving a compact arrangement of small pulleys. The double sided drive belt causing the upper plate of the centrifuge to turn in the same direction as the components that turn at one half the speed.

In another aspect of the invention, automated syringe pumps load and unload syringes inserted into the apparatus. A geared motor assembly drives a rotating lead screw that moves a pusher mounted at the end of a rod. A spring-loaded drive nut mounted on the rod rides along the lead screw to advance and retract the rod and pusher. The spring-loaded drive nut can be disengaged by manually rotating the pusher. This allows the operator to manually advance or retract the rod in a disengaged position as a syringe is placed into the apparatus or removed from the apparatus. When the operator releases the pusher, the drive nut locks onto the drive screw and will then only move when the drive motor is activated.

In another aspect of the invention, a centrifuge is provided with automatic level detection. A sensor is operated by means of light or other energy that will travel through plastic and blood plasma but not through red blood cells. For example, sending and receiving fiber optic conduits terminate in lenses mounted on the housing near the centrifuge and transmit and receive light or other energy. The transmitted signal is received and transmitted into first and second light pipes carried on a caddy mounted to the centrifuge as the centrifuge rotates. A separation canister is mounted in the caddy with a portion of the canister located between the first and second light pipes. When the interface between the red blood cells and plasma in the canister moves past the location of the light pipes, the signal will be received by the second light pipe and transmitted back to the sensor. Once the level is sensed, that signal can be used to control various aspects of automated processing. For example, once the sensor detects the level of the plasma interface, the machine can then turn the syringe pump off. Additional sets of light pipes can also be used on the caddy at another portion of the separation canister.

DETAILED DESCRIPTION OF THE PREFERRED EMBODIMENTS

Figure 1:
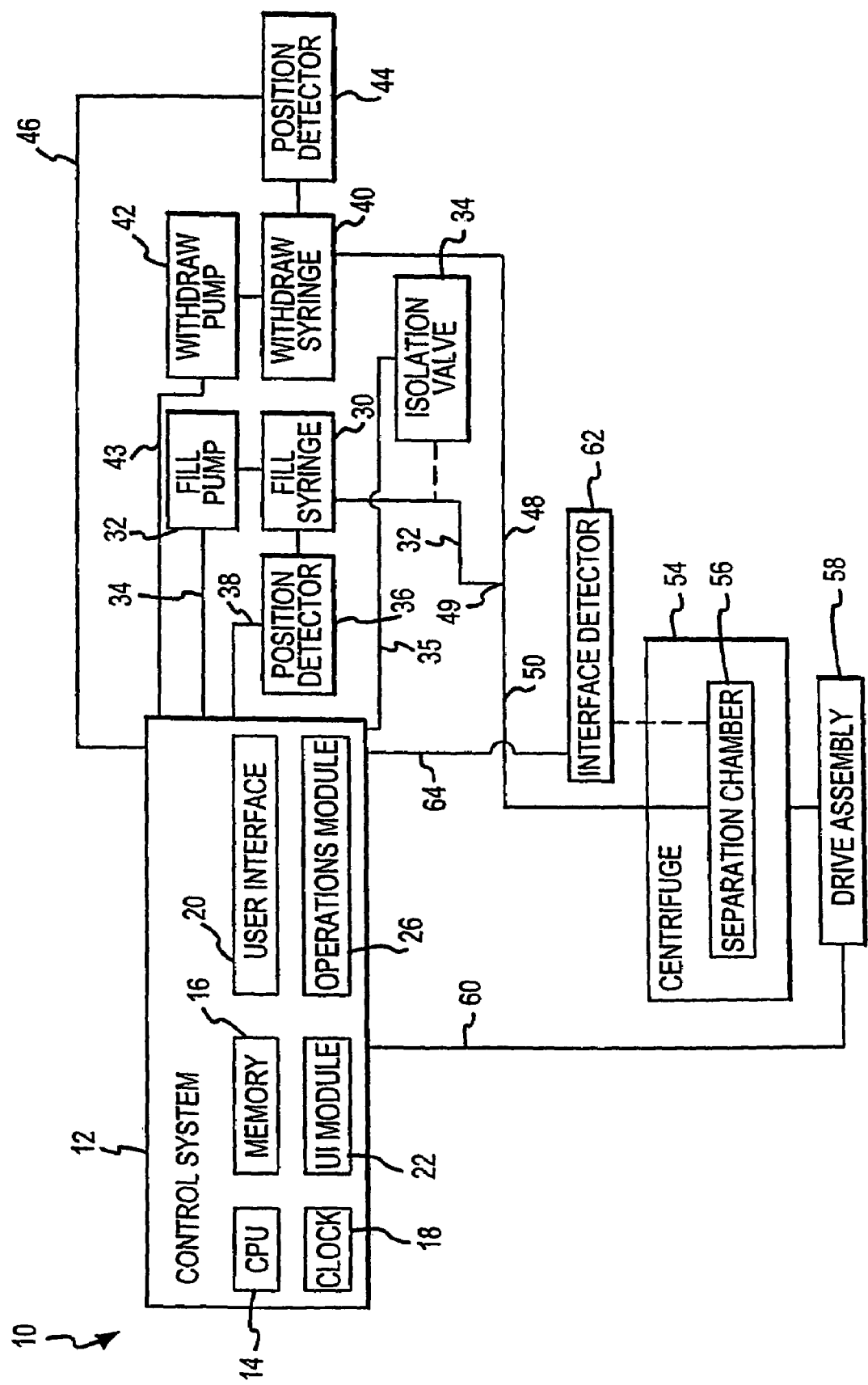
FIG. 1 illustrates in block diagram form a blood separation and fraction collection system according to the present invention.

Generally, the invention is directed to a blood separation and collection system useful for automated separation of blood into its component parts and for collection (based on user input) of platelet rich plasma (PRP) and, in some cases, platelet poor plasma (PPP) or white blood cells. In operation, the operator prepares the system by unlatching a centrifuge door and inserting a separation chamber portion of a separation and collection disposable onto a caddy mounted to the top of a centrifuge. Tubing is included as part of the disposable for inputting or filling blood into the chamber and for withdrawing or collecting blood components from the chamber and typically has connectors on one end for connecting to fill and withdraw syringes and is connected on the other ends to an inlet/outlet port on each side or half of the two-part chamber. The syringe connector end of the tubing is first advanced into an aperture in the caddy and through an upper aperture in the center of the centrifuge. A diverter in the centrifuge aperture assists in creating a tube path in the centrifuge and threading the tubing through the aperture to a side window in a shield or sidewall of the centrifuge. As the tubing emerges from the window, an operator grasps it and draws it through the window. The separation chamber portion of the disposable is snapped into a cradle on the caddy with portions, e.g., nipples, of each half or segment of the separation chamber residing between light pipes mounted within a level detection assembly on the caddy to allow light to be passed through blood in the chamber halves to detect interfaces between separated components.

A portion of the tubing forming a loop in the separation chamber assembly is placed into a tubing trough or recess and tubing retainers on an upper surface of the caddy. A tubing clamp or connector in the tubing of the disposable that has been drawn or pulled through the centrifuge is placed into a clamp or tube latch at an end of a tube positioning arm extending from a wall of the centrifuge housing. The arm holds the portion of the tubing retained by the tubing clamp so as to position and support the tubing above the centrifuge and generally in a position that is coaxial with a central axis of the centrifuge. In one embodiment, a tapered portion of the tube clamp is lubricated prior to insertion in the latch to control heat buildup and wear on the tube clamp during operation of the centrifuge. The disposable includes a run of tubing above the arm and tube clamp that includes a branch connection, such as a Y-connector, that leads to a fill tube with a syringe connector and a withdraw tube with a syringe connector. The operator places a portion of the fill tube above the Y-connector into an isolation valve, e.g., an electrically-activated pinch valve, that is located adjacent to two syringe recesses in the upper housing assembly of the device.

With a syringe cover of the upper housing assembly in the open position, the operator places a fill syringe, such as a large conventional syringe, containing blood in one of the syringe recesses adapted for that size of syringe and connects the syringe to the fill tube connector. The operator also positions the flat end of a plunger of the fill syringe into a recessed surface of a knob or pusher portion of a syringe pump assembly. In one embodiment, the pusher or know is rotated until a drive nut disengages from a drive screw in the pump and then the operator manually adjusts (e.g., pulls and/or pushes on the knob) a position of a shaft or rod connected to the knob until the pusher or knob recessed or engagement surface is at the proper position to engage the end of the plunger. In one embodiment, springs or other devices are used in the drive nut or elsewhere in the pump such that the recessed portion of the pusher engages the end of the syringe plunger when the operator releases the know as the pusher is automatically returned to its operating or at-rest position and the drive nut engages the drive screw. Similarly, an empty fill syringe, e.g., smaller conventional syringe is also attached to the connector of the withdraw tube and inserted into the second, smaller syringe recess. As the operator inserts each of the syringes into the recesses, an optical syringe detector is interrupted and thereby, detects the presence of each syringe in the recess.

The syringe detectors are used by the system to indicate to the operator that the syringes are properly positioned in the recess by responding to the interrupted detector signal to activate an indicator light on a syringe indicator display that includes LEDs or other indicators representing each of the syringes. In most preferred embodiments, detection of the absence of either syringe in the recesses by the system is used by a controller or control system of the separation and collection system to initiate steps to disable the device from operating. The syringe cover assembly and the centrifuge cover assembly are both then closed by the operator. A centrifuge door latch indicator, such as an LED, may be used by the control system to indicate to the operator that the centrifuge cover has been properly latched. Similarly, an indicator on the syringe indicator display may indicate that the syringe cover has been closed. The control system may further operate to respond to detection of the failure of the centrifuge door to latch properly by disabling the system from operation.

The operator then employs a user interface on the centrifuge cover assembly to set a desired volume of platelet rich plasma to be delivered into the second, smaller syringe. The user interface includes a keypad, a display, and a series of progress LED indicators that indicate to the operator the progress of blood processing. In one embodiment, the operator sets the desired volume of platelet rich plasma by pushing appropriate keys on the keypad to increment or decrement a volume value displayed by the control system on a screen of the display. When the amount appearing on the display screen is the amount desired by the operator, the operator pushes a start button on the keypad. Once the start button is pushed, separation of the blood in the fill syringe into platelet rich plasma (PRP) and PRP deposition into the second, smaller syringe is entirely automatic and requires no operator intervention with operation of the centrifuge and syringe pumps being controlled by the control system hardware and software. However, if the operator should desire to stop the process, a stop button on the keypad can be activated. At the conclusion of the automated process, the platelet rich plasma is in the smaller syringe and the unused blood and the balance of the contents of the separation chamber, including the platelet poor plasma, are in the larger syringe. The operator may then remove the smaller syringe from the system for use and also remove and discard the larger syringe. Caps are then applied by the operator to each of the tube syringe connectors and the disposable including the separation chamber and tubing is removed from the system by reversing the process used to install it. In addition to the production of PRP, the operator can also recover the platelet poor plasma (PPP)

separated by the system. During the automated cycle, the operator is prompted by the control system via the user interface, and the operator may then elect to push a PPP button on the keypad to deliver the PPP to a third syringe that may be installed in one of the syringe recesses.

Figure 2:
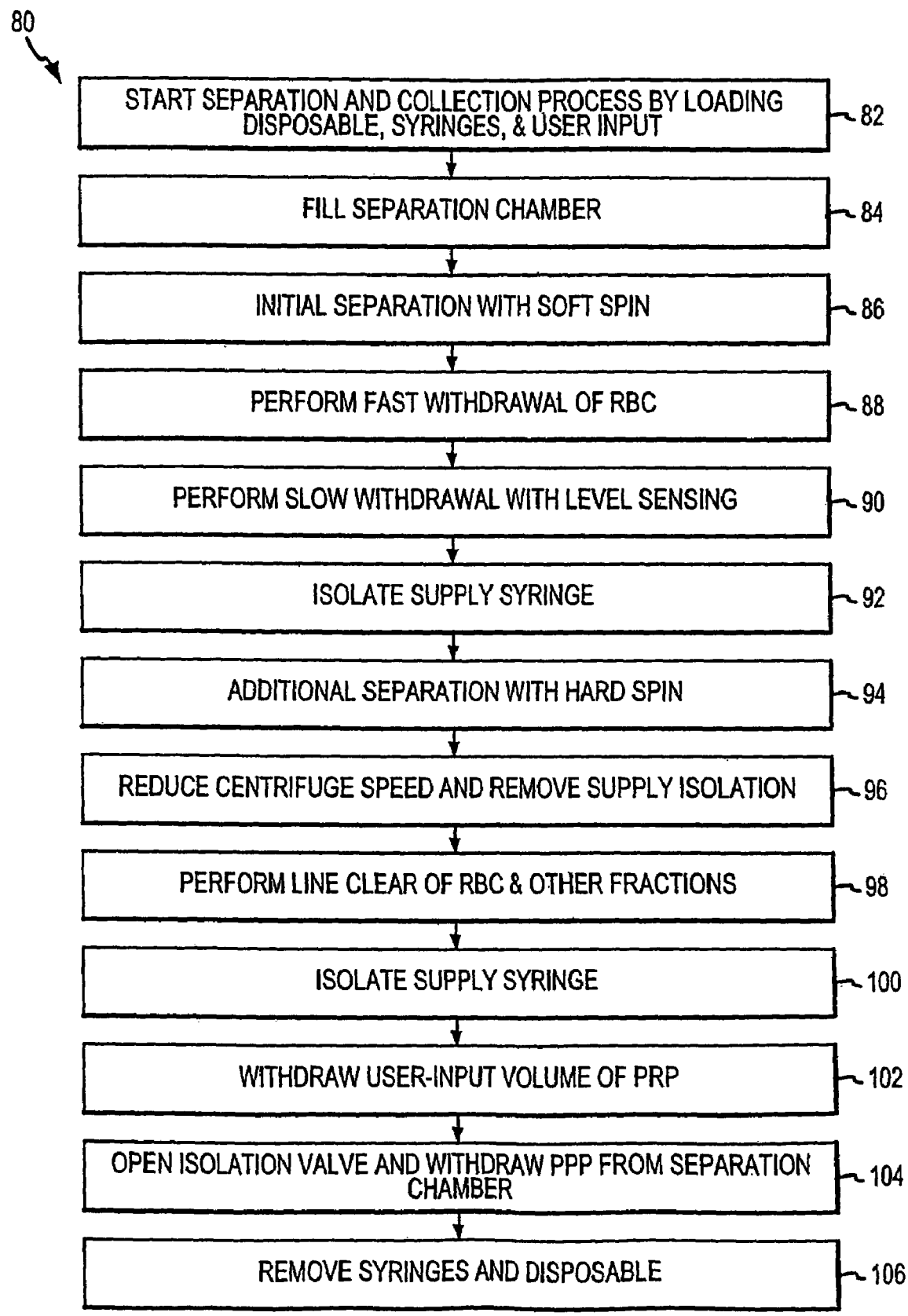
FIG. 2 is a simplified flow chart illustrating functions performed by a blood separation system (such as the system of FIGS. 1 and 3-21) during an exemplary separation and collection process.

The above description provides a brief overview of some of the unique features of separation and collection systems according to the invention and at least provides a context for explaining in more detail separation and collection processes provided (typically automatically) by such systems. The following description begins with a general description of systems configured according to the invention with reference to FIG. 1. Referring then to FIGS. 1 and 2, a detailed explanation is provided of separation and collection processes of the invention stressing the unique functions and abilities of such systems in collecting desired fractions or components from blood with a compact and easy-to-operate device. Once the functions and operation of systems according to the invention is understood, the description then turns to a specific discussion of the physical components that are used in one exemplary embodiment to provide the desired features and functions. In this regard, FIGS. 3-22 illustrate in detail the components of a collection separation and collection system.

FIG. 1 illustrates in functional block form a blood separation and collection system 10. As illustrated, a control system 12 is provided to control automated operation of the system 10 and includes a central processing unit (CPU), e.g. one or more microprocessors and/or chips performing the logic, computational, and decision-making functions including interpreting and executing received instructions and managing data storage. The control system 12 includes memory 16 for storing digital information (such as user input PRP collection volumes) and a clock 18 used by the CPU 14 (or operations module 26) to measure lengths of certain separation and collection processes, as explained in detail with reference to FIG. 2. A user interface (UI or, in some embodiments, a GUI) 20 is provided to allow operators to monitor operations of the system 10 and to enter input to "program" the system 10 to perform certain operations. For example, the user interface 20 may include a start button and a stop button to control operations, a display screen to allow the CPU 14 to display to the operator information regarding current operations (such as time left in a specific portion of the process or a user-input collection volume), indicators such as LEDs to indicate operations such as whether a centrifuge or a syringe cover is closes, a syringe is properly installed, stages of operation, and the like, and a keypad or other input device (such as a touch screen, audio command input device, and other well-known input devices) to allow the operator to enter information at prompts (such as a PRP collection volume, a command to collect PPP, and the like). These various components of the UI 20 may be located at different locations within the system 10 as appropriate, such as indicators near the device or component being operated and display and input device adjacent each other at a user-friendly or ergonomically-desirable location in the system 10. A UI module 22 is provided to control operation (in conjunction with CPU 14 and memory 16) of the UI 20. An operations module 26 is provided to control most other operations (such as operation of the centrifuge drive and inlet and outlet pumps) of the system 10. The modules 22 and 26 typically are embodied in software that is executed by the control system 12 but may also include hardware components and in some cases, separate CPUs or processors and/or memory are provided for each module 22, 26.

The system 10 includes a fill syringe 30 (or other fluid container) that is typically installed manually by an operator and initially contains blood that is to be processed by the system 10. A fill pump 32 is provided to pump fluids to and from the fill syringe 30 and is operated by the control system 12 via signal line 34. In one embodiment, the fill pump 32 is a syringe pump connected externally to the fill syringe 30 to selectively move a syringe plunger to force fluid out of the syringe 30 or to pull or draw fluid into the syringe 30. A position detector 36 is provided to monitor for the presence of the fill syringe 30 in the system 10 (such as with a light or other energy beam or electrical contacts) and transmits a signal on an ongoing basis to the control system 12 and operations module 26 via signal line 38. A fill line 32 (such as a single lumen tube) is used to fluidically connect the syringe 30 to a centrifuge 54. An isolation valve 34 (such as a pinch valve or other useful valve arrangement) is provided to control flow in the line 32 and is controlled again by the control system 12 and operations module 26 via signals on line 35.

Similarly, a withdraw or collection syringe 40 is provided (and typically installed by an operator) and is in fluid communication with the centrifuge 54 via collection or withdraw line 48 (again, typically, single lumen tubing). The fill and collection lines 32 and 48 meet at a connector 49 (such as a Y-connector) and become a single fluid line or fill/withdraw line 50, which in most preferred embodiments is a single lumen tube. A withdraw or collection pump 42 is provided to draw fluid into the syringe 40 and controlled by the control system 12 and operations module 26 via signals on line 43. When syringes are used for syringe 40 (instead of other containers), the pump 42 is typically a syringe pump. A position detector 44 transmits signals over line 46 to the control system 12 (which in response operates syringe indicators such as colored LEDs) in response to the presence or absence of the syringe 40.

The centrifuge 54 is included in the system 10 to receive blood or other fluids from the fill syringe 30 and to rotate to separate by centrifugal forces components (such as red blood cells, white blood cells, and platelets) from the blood or other fluid and then to be configured to facilitate selective withdrawal or collection of such separated components. The centrifuge 54 is driven by a drive assembly 58 that is selectively operated, and at desired rotation rates or speeds, by the control system 12 and operations module 26 via signals on line 60. Although not shown, a velocity detector may be provided to transmit signals in response to the rotation of the centrifuge 54 to the control system 12, which can respond by increasing or decreasing the centrifuge speed to maintain the centrifuge 54 within an acceptable operation range. The fluid line 50 is fed into the centrifuge 54 and connected to a separation chamber 56 to provide a flow path to and from the separation chamber 56. As will be explained in detail below, the separation chamber 54 is preferably a two-chambered or halved container that has a single port for inputting fluids and withdrawing fluids or separated fractions. During operation, it is important to be able to determine interfaces between these separated fractions or component rich portions of the fluid in the chamber 56. An interface detector 62 (such as an assembly that transmits light or other energy through the chamber 56 and contained fluid) is provided to monitor separation processes and to transmit signals via line 64 to the control system 12 and operations module 26 for processing and responsive control of the drive assembly 58 and pumps 32, 42. To explain how the components of system 10 operate to provide effective and selectable processing of blood or other fluid samples, the operation of the system 10 will now be explained in detail with reference to FIGS. 1 and 2.

A separation and collection process 80 performed according to the invention with the system 10 or similar system is shown in FIG. 2. As shown, the process 80 begins at 82 with loading or installing a disposable and syringes (such as fill syringe 30 containing blood to be processed and withdraw syringe 40 to collect PRP) and entering user input. The disposable referred to in 82 generally includes all tubing 32, 48, 50 and connectors (such as connector 49 and any tube clamps and the like) and the separation chamber 56. In this manner, all fluid contacting surfaces and components (including the syringes 30, 40) can readily be removed from the system 10 after use to avoid contamination or the need for cleaning components within the system 10. The disposable is installed by feeding syringe connectors and tubing 32, 48, 50 through the centrifuge 54 and positioning the chamber 56 along with a certain length of tubing on a caddy device (explained in detail below) that is mounted to the top of the centrifuge 54. The tubing 50 is held in position above the centrifuge 54 on latch of a positioning arm (again explained in detail below) and the tubing 32 is connected to the isolation valve 34 and tubing 32, 48 are connected to the syringes 30, 40. The syringes 30, 40 may be a number of sizes but in one embodiment are a 60 cc and a 10 cc syringe, respectively, that are inserted into recesses in the system 10 adjacent the syringe positioning detectors 36, 44. The fill syringe 30 contains a volume of blood to be processed and the withdraw syringe 40 is empty to provide a collection receptacle for PRP during processing.

Also, at 82, an operator inputs user input such as a volume of PRP to be collected in the syringe 40 and/or a command that PPP be collected at the end of processing. In one embodiment, messages are displayed to the operator on an instrument display portion of the UI 20, such as in rows having a set character per row (e.g., 2 rows with 20 characters/row). During the process 80, the UI module 22 can operate to display a time remaining in the overall process 80 and the PRP volume to be withdrawn (a default volume or the volume input by operator) or a PRP volume already withdrawn (such as after completion of that withdrawal step). Operation status may also be provided on the display. Status may include messages indicating a system error that has terminated the process (i.e., stopped the centrifuge 54, stopped both syringe pumps 32, 42, opened the isolation valve 34, and unlocked the centrifuge door or cover) and the message typically would provide an error number or identifier and instruct the operator to contact maintenance personnel and visual displays may be accompanied by audio indication of a system error. Messages indicating that user intervention is required are also displayed on the display or elsewhere in the UI, such as load syringe, close cover(s), press start, and the like.

System status messages are also provided throughout the process 80 by the UI module 22 on UI 20. In one embodiment, the system status messages are displayed on the display (e.g., to indicate which operation is occurring such as filling, withdrawing or collecting, and the like) along with progress LEDs or other indicators to give an approximation of a portion of completion of the current step or function (such as by using 4 LEDs that light as each fourth of the operation is completed and flash as a particular fourth of the operation is being performed). Additionally, red and green LEDs may be provided in the UI 20 to allow the UI module 22 to report to the operator when the centrifuge cover is open or closed, when the syringe cover is open or closed, and when the syringes 30, 40 are properly positioned in the system 10. The UI 20 may include minus and plus keys to facilitate inputting or changing the PRP collection volume and a PPP key may be provided or an accept key to allow the user to choose to collect PPP after PRP collection is completed.

Returning to step 82, after the system 10 completes a self-check and performs initialization (or after a previous separation cycle), a "STOP" button or indicator in the UI 20 is lit by the UI module 22 and the progress LEDs are turned off. The UI module 22 displays a message indicating that the operator is required to load the system 10 (i.e., insert the disposable, the syringes, and close covers), enter a PRP volume (or accept a default), and then press the "START" button or input a start command. The PRP default volume (such as 0 to 10 cc when a 10 cc collection syringe 40 is used) is initially displayed at 82 by the UI"module 22 on the UI" 20 and the operator then accepts this default or indicates a desired volume (such as by pressing arrow keys or plus/minus keys).

The operator then presses the "START" button or otherwise initiates further processing by the system 10 and a time for completion is displayed by the UI module 22 on the UI (based on calibration processes for the system 10 including particular fluids and volumes) and is updated by the UI module 22 based on actual completion times and/or based on calculated or calibrated completion times. For example, the system 10 may be calibrated to perform separation and collection processes in 17 minutes based on collection of a maximum volume of PRP and collection of PPP but if less PRP is desired or collection of PPP is deleted the UI module will function to reduce the completion time displayed. In some embodiments, the operator is allowed to change the PRP volume at any point in the process 80 prior to collection of or completing collection of PRP. The control system 12 continues to monitor operating status including position or presence of syringes and whether covers are properly closed throughout the process 80 and when necessary, to interrupt operation such as when the syringe cover is opened during fill or withdraw operations. The control system 12 will also verify system status prior to proceeding from step 82 to step 84 (such as whether the syringes 30, 40 have been properly positioned) and if some intervention is required by the operator, the UI module 22 will operate to display the proper intervention message on UI 20.

At 84, the system 10 operates to fill the separation chamber 56 with fluids in the fill syringe 30. Initially, the UI module 22 displays a message indicating that filling is proceeding and lights (or flashes) a first progress LED or indication light. The operations module 26 operates the drive assembly 58 to ramp the centrifuge 54 up to a dwell rate, such as 900 to 1100 revolutions per minute (RPM) or as in one embodiment, 940 to 1060 RPM, with ramping occurring at a controlled at a specific slew rate such as at a rate of 250 RPM/second. Concurrently, the fill pump 32 is operated by the operations module 26 to force or pump the blood from the fill syringe 30, such as at a rate up to 40 ml/minute or higher, with the operations module 26 operating the pump 32 until an ending-fill position is detected and a corresponding signal sent on line 34. Ending-fill position in one embodiment is detected through the use of a switch in the pump that detects the position of a drive nut or a drive shaft which are linked to the end of the plunger of the syringe 30, with the switch being positioned and pump 32 selected to effectively operate a particular size syringe (such as a standard 60 cc syringe or other known size syringe having standardized dimensions including syringe length and plunger positions and lengths). If the ending-fill position is not detected after a set period of time (such as within 10 minutes), the operating module will indicate a fill syringe 30 or fill pump 32 error and at least temporarily stop the process 80. After successful completion of step 84, the separation chamber 56 (and more often, the two halves or portions of the chamber 56 that are used to enhance self-balancing within the centrifuge) are at least partially filled with blood which due to the relatively light centrifugal forces at the dwell rate is positioned externally in the chamber halves but typically is not separated into components. In some embodiments, when either syringe pump 32, 42 is operating an LED or other indicator is operated by the control system 12 to indicate the operation of the pump 32, 42.

At 86, the system 10 operates automatically (without operator intervention) perform an initial separation of the components in the blood in the chamber 56. After the syringe 30 is emptied to a desired level, a status message indicating that the current operational phase is "processing" and the second and first progress indicators are lit. The operations module 26 operates the drive assembly 58 up to a soft spin rate, e.g., a rate useful for creating enough centrifugal forces to separate red blood cells (RBCs) to plasma in the outer regions or portions of the chamber halves or segments with minimal mixing of other components in the heavier RBCs (such as white blood cells and platelets). In one embodiment, the soft spin rate is selected to be about 2800 RPM plus or minus 150 or more RPMs. Again, the change in centrifuge rotation rate is performed at a slew rate (such as less than 250 RPM/second). After the soft spin rate is reached by the centrifuge 54, the centrifuge 54 is operated for a length of time at the soft spin rate to achieve a desired level of initial separation. In one embodiment, the soft spin rate is maintained for at least about 4 minutes (but of course this time period can be varied to successfully practice the invention and may vary with blood content (human versus animal), for volumes processed and dimensions of the chamber, and to account for other operational factors and variables).

At 88, after the initial separation period has passed, the centrifuge 54 is slowed at a slew rate (e.g., less than 250 RPM/second) to a dwell rate, e.g., about 2800 RPM plus or minus 150 RPM, to allow more effective withdrawal of separated fluids and components. After the centrifuge 54 has reached the dwell rate, the fill pump 32 is operated in the opposite direction or manner to cause fluid, i.e., RBC-rich plasma, to be drawn from the separation chamber 56 (from the two ports) through the line 50 and fill line 32 into the now substantially empty, fill syringe 30. The system 10 is configured for processing a known blood content or range of contents, and as such, a known or safe percentage of the blood sample can be withdrawn at a faster withdrawal rate without concern for detecting an interface between the RBCs and the next fraction. For example, for human blood, the inventors have determined that at least 25 percent of blood sample that has been initially separated with a soft pack (as described for step 86) can be withdrawn to quickly remove RBC-rich plasma. The volume to be withdrawn can vary with fill volume, i.e., safe percentage times the fill volume (such as 25 percent of about 60 cc or 15 cc).

Significantly, some embodiments of the process 80 call for self-calibration of the system 10 during the fast withdrawal of 88. This is an important feature of the process 80 as the system 10 can be calibrated for a particular patient or sample of blood, for a particular system 10 configuration (i.e., operations may slightly vary based on variations or tolerances in the fabrication of sensor parts, centrifuge parts and operation, for different separation chambers 56, and other parameters). Hence, self-calibration in a just-in-time fashion is often useful for successfully detecting the RBC/plasma interface in the current sample. As discussed above, the range of human hematocrit levels is well documented such that it is known that the interface cannot be present and detected by the interface detector 62 during fast withdrawal 88 (unless there is improper volumes or improper loading of the device).

Based on this fact or knowledge, self-calibration of the system 10 for the current patient or sample is performed during fast withdrawal 88 by collecting and analyzing sensor signal data received from an optical sensor in the detector 62. Typically, this analysis involves estimating a running mean and a running standard deviation (although other analysis can be performed). Using the results of the real time analysis (i.e., the calculated mean and standard deviation) the response of the detector 62 in absence of the interface is characterized. In other works, the self-calibration process at 88 involves determining the output of the optical sensor or other sensor in the interface detector 62 for the current blood sample (or current patient), for the system 10 configuration, and for the particular process 80 (e.g., in some cases, operation of a system 10 may vary slightly over its operating life). Interface detection can now be performed based on this calibrated output signal or expected signal based on the characterization during fast withdrawal 88.

With the volume known by the control system 12, the fill pump 32 is operated at 88 to withdraw this known volume (with a syringe or other pump being used for pump 32 that is able to effectively be calibrated for withdrawing a known volume into syringe 30), such as by withdrawing the syringe plunger a known distance. The withdrawal can be performed in this step 88 at a relatively fast rate, such as greater than about 30 ml/minute, as an interface is not being detected and used to control operations (but rather a movement of the syringe pump drive is used). However, the operations module 26 monitors signals from the interface detector 62 (e.g., the RBC to plasma interface sensor). A positive detection or indication of the interface at this time typically indicates that the chamber 56 is not properly positioned or is not filled or that there is a sensor 62 problem, which the operations module 56 uses to trigger a system error (with corresponding message on the display and/or termination of operations of the system 10).

After completion of the fast withdrawal of RBC, the process 80 continues at 90 with the slow withdrawal of RBC or RBC-rich plasma from the chamber 56 using level or interface detection to provide a completion point. During slow withdrawal, the centrifuge 54 is maintained at the dwell rate but the speed of withdrawal of fluid and RBC is significantly reduced to enable the RBC/plasma interface to be detected and the operations module 26 to respond by stopping the syringe fill pump 32. The slow collection or withdraw rate is selected to minimize the risk of withdrawing too much fluid while still allowing efficient operations, and in one embodiment, the slow withdrawal rate is selected from the range of about 4 to 6 ml/minute by operating the fill pump 32 to move the fill syringe 30 plunger outward at a corresponding rate. Once a positive detection is determined from the signal provided by interface detector 62 (which, in one embodiment, includes light pipes and/or lenses located adjacent to nipples in the chamber halves as will be explained below), the operations module 26 stops operation of the fill pump 32 via a signal on line 34.

The level detector 62 and operations module 26 may be calibrated or programmed in a number of ways to "detect" the interface between the separated RBC and plasma. In one embodiment, a trigger level or calibration level (as discussed in step 88) is set by first detecting the presence of a signal prior to fill when there is nothing blocking the light or sensors. During fast withdrawal, a sensor mean signal is determined when it is known that RBC are adjacent the light pipes or other sensors and there is no signal being generated as the RBC block the light or sensing energy and then a standard deviation is determined to evaluate the noise level seen or sensed by the detector 62. The sensor or interface trigger level is then set at the mean plus a number of deviations (such as 1 to 8 or more deviations) to provide a trigger level that has a relatively low probability of generating false positive detects. Of course, other algorithms can be used to set the interface between the RBC and plasma, and the described methods are considered adequately broad to cover such operations.

A positive RBC/plasma interface detection then is set to occur when one or more trigger levels are identified within a set time interval, such as 4 trigger level signals within intervals of 30 milliseconds, 60, milliseconds, or some other useful time interval. In other words, the system 10 looks for a sensor response at the interface detector 62 that cannot be accurately represented by the characterization of the signal collected during the fast withdrawal 88, and when this occurs (or after it occurs repeatedly), the position of the blood in the chamber 56 is marked as the interface between the RBCs and the plasma. The intervals are based on the rotation of the centrifuge and when light from a source outside the rotating centrifuge 54 is transmitted through the light pipes adjacent the chamber 56 (i.e., once a rotation in each pipe or twice each rotation because of the use of a two chamber or halved separation chamber 56 and two sets of light pipes) and is determined based on the dwell rate or rotation rate of the centrifuge 56. So, at 1000 RPM, one embodiment of the centrifuge 54 rotates one revolution in 60 milliseconds such that the interface detector 62 is able to provide a detection signal on line 64 twice per revolution or every 30 milliseconds.

Once these calibration steps are performed (and can be performed once at a first run of the system 10 or more preferably, are performed on an ongoing basis each time a separation process 80 is completed to increase accuracy of interface detection), any positive detection of an RBC/plasma interface during slow withdrawal at step 90 is most likely based on light of a sufficient quantity passing through the chamber 56 and the fluid in the chamber 56, e.g., through PRP rather than RBC. The use of positive triggers in multiple or sequential time intervals (such as 4-30 millisecond intervals or two rotations of the centrifuge 56) is useful for more accurately positioning the interface(s) in the halves of the chamber 56 over the sensor or light pipe location.

The process 80 continues at 92 with operation of the isolation valve 34 by the operations module 26 via a signal on line 35. The isolation valve 34, e.g., a pinch valve contacting the outside walls of the tube 32, is closed to block flow in fill line 32 and to isolate the fill syringe 30. Isolation is utilized to maintain the current location of the RBC/plasma interface within the chamber halves, as without isolation fluid pressures and other factors may move the interface causing later processing to be less effective in collecting all or a large percentage of the separated PRP with minimal inclusion of RBC. The operations module 26 will not proceed further until it senses that the isolation valve 34 has closed. At 94, the process 80 continues with additional separation at a hard spin rate that is higher than the soft spin rate and is selected to force the red blood cells and other components to separate further from the platelets and to collect or pack (without forming a plug) within the most outer portions of the chamber 56. In one embodiment, the hard spin rate is selected from the range of about 3500 to 4000 RPM or higher and preferably about 3800 RPM. At 94, the operations module 26 operates the drive assembly 58 to ramp up the speed of the centrifuge 56 at a slew rate (such of about 250 RPM/second) from the dwell rate to the hard spin rate. The level detector 62 is typically not used at this point to determine the amount of time to continue step 94 but instead experimentation and knowledge of typical blood content (e.g., for different species such as humans, bovine, and the like) and characteristics and the configuration of the chamber 56 has allowed a minimum hold time to be determined. For example, the minimum hold time can be set at about 6 minutes (or some shorter period of time) to obtain desired levels of additional separation.

After the minimum hold time, at 96, the centrifuge speed is reduced by a slew rate down to a dwell rate (such as 1000 RPM) to facilitate removal of additional RBC and other components (such as white blood cells). Note, that in some embodiments, white blood cells are collected by utilizing only a soft spin or single spin from 0 to about 2200 RPM and more preferably about 1200 to 2000 RPM without an additional hard spin. Once the dwell rate is obtained at the centrifuge 56, the operations module 26 operates the isolation valve 34 to open to remove the isolation of the fill syringe 30 and the process 80 is not continued until the operations module 26 senses the isolation valve 34 has been opened (and fluid can again be drawn into the fill syringe 30).

At 98, the line 50 (and typically portions of the chamber 56) is cleared of RBC and other undesired fractions (such as white cells). Clearing is performed based on the removal of a line clearing volume of fluid. The line clearing volume may be determined by a combination of volumetric calculations for the disposable arrangement employed in the system 10, including the volume of fluid in an outer portion of the chamber 56 having RBC and other undesired or non-platelet components and in the tube 50 (e.g., the tubing in the disposable between the chamber 56 and connector 49), and experimentally collected information. In one preferred embodiment, the line clearing volume is set at 1 ml plus or minus 0.1 ml of fluid, but the line clearing volume of course should be selected to match the disposable configuration to successfully practice the method 80 and to collect a large of volume of "clean" PRP. Line clearing at 98 is performed by the operations module 26 operating the fill pump 32 via line 34 to draw the line fill volume of fluid into the fill syringe 30 (and out of tube 32 and 50 and in some cases, chamber 56). After withdrawing the line clearing volume, the pump 32 operation is terminated and at 100, the operations module 26 again operates the isolation valve 34 to isolate the fill syringe 30 from line 50 (and line 48 and collection syringe 40).

At 102, the operation module 26 operates the system 10 to withdraw the user input volume of PRP and at this point a third progress indicator or LED is lit on the UI 20. To collect the separated PRP, the operations module 26 retrieves the user input volume of PRP and then operates the withdraw or collection pump 42 to fill the withdraw syringe 40 (such as by moving the plunger outward) at a PRP collection rate (such as in the range of about 10 to 20 ml/minute or other useful rate). The PRP collection at 102 is a volumetric withdraw and when the pump 42 has withdrawn the input volume (typically 3 to 10 ml) the operation module 42 terminates operation of the pump 42. The PRP collection volume is preferably set within a range based on the input or fill volume and for the particular blood content (e.g., human versus another species or blood content). In one implementation of the system 10, a 60 cc supply of blood is provided which typically contains at least 10 cc of PRP after the above described separation processes. Hence, the user input PRP collection volume can be set at any volume less than 10 cc (or other known "safe" volume of PRP that is unlikely to contain any significant amount of platelet poor plasma (PPP) from the chamber 56). The PRP being drawn into the withdraw syringe 40 is pulled or suctioned from the tube 50 and from the chamber 56 (when the collection volume is not exceeded by fluid in the tube 50 which is typically the case in practice). Additionally, if an end position of the withdraw syringe 40 is detected (such as by a switch in the withdraw pump 42), the withdraw operation is also terminated (as sometimes occurs if a the input collection volume coincides with the volume of the syringe 40, e.g., 10 cc and 10 cc, respectively).

At 104, a fourth (and final) progress indicator or LED is lit and a status message indicating the current phase is the emptying phase is displayed on the UI 20. The operation module 26 determines if the operator has selected the optional collection of PPP, such as by pressing a PPP pause or collection button or key. If PPP collection is not selected, the isolation valve 34 is opened to allow fluid to flow to the fill syringe 30 and the pump 32 is operated to withdraw, such as at a rate of 40 ml/minutes or greater, the remaining (or at least a large portion of the) fluid in the tube 50 and chamber 56, i.e., the PPP. Typically, the pump 32 is operated until the end position is detected (such as by a switch in pump 32) indicating the plunger has been fully withdrawn (e.g., to the initial fill position). If the PPP is to be collected, the operator is allowed to open the syringe cover without an error alarm or message and to remove the fill syringe, which contains RBC-rich fluid, and replace the syringe 30 with a PPP collection syringe (not shown in FIG. 10) in the same location and connect the syringe to the fill line 32. The operator is then prompted on the UI 20 to press the "START" button to indicate that the fill syringe 30 has been replaced with a PPP collection syringe (or in some embodiments, to indicate that PPP has been manually withdrawn from either syringe location 30 or 40). Once the "START" button is pressed, the operations module 26 verifies that syringes 30 and 40 are loaded and if not, then the centrifuge 56 is slowed to a stop and the STOP light is lit. If the syringes 30 (a PPP collection syringe) and 40 are loaded, then the pump 32 operates the fill syringe 30 until the end withdrawal or end position is reached (as sensed by a switch or other techniques) or a preset time is reached (such as 10 minutes or less) at which point the centrifuge 56 is stopped and the "STOP" indicator or button is lit to indicate the end of centrifuge, separation, and collection operations. At 106, the syringes 30 and 40 and the disposable including chamber 56 and tubing 32, 34, 50 are removed from the system 10.

The operation of the system 10 and, specifically, the centrifuge 54 and the attached chamber 56 has been explained in terms of rotation rates that have proven useful for obtaining desired blood separation and facilitating collection of portions of such separated blood. However, the specific rotation rates will likely vary with differing sizes, i.e., diameters, of the centrifuge and/or the chamber. It should be understood that separation of blood is obtained by rotating the centrifuge 54 and chamber 56 at rates high enough to generate adequate centrifugal forces to cause particles within the blood to be pushed away from the central axis of the centrifuge 54 within the chamber 56. Hence, it may be appropriate to provide ranges of g's that correspond to the above rotation rate ranges or values for an embodiment of the centrifuge 54 and chamber 56 that has been tested by applicants. Based on calculations, for a chamber that has a 3-inch radius from the center to the end of the nipple, the g's at 1000 RPM is 86, at 2000 RPM is 343, at 2500 RPM is 538, at 3200 RPM is 880, and at 4000 RPM is 1375. For other sizes of the chamber 56 and/or centrifuge 54, different rotation rates may be required or useful in obtaining g's similar to those listed above to achieve a desired separation of a liquid sample such as blood.

While a number of arrangements can be used to practice the invention, FIGS. 3-22 illustrate an exemplary blood separation and collection system 110 that can be used to implement the separation and component collection process 80 described with reference to FIG. 2. The system 110 is a compact (about 18 inches wide by 13 inches in height by 17 inches in depth) device that is designed to be self-contained, to be quiet with minimal vibration, and to provide automated processing and collection (as described for process 80). The components that contribute to these features of the system 110 are highlighted and discussed in detail in the following paragraphs.

Figure 3:
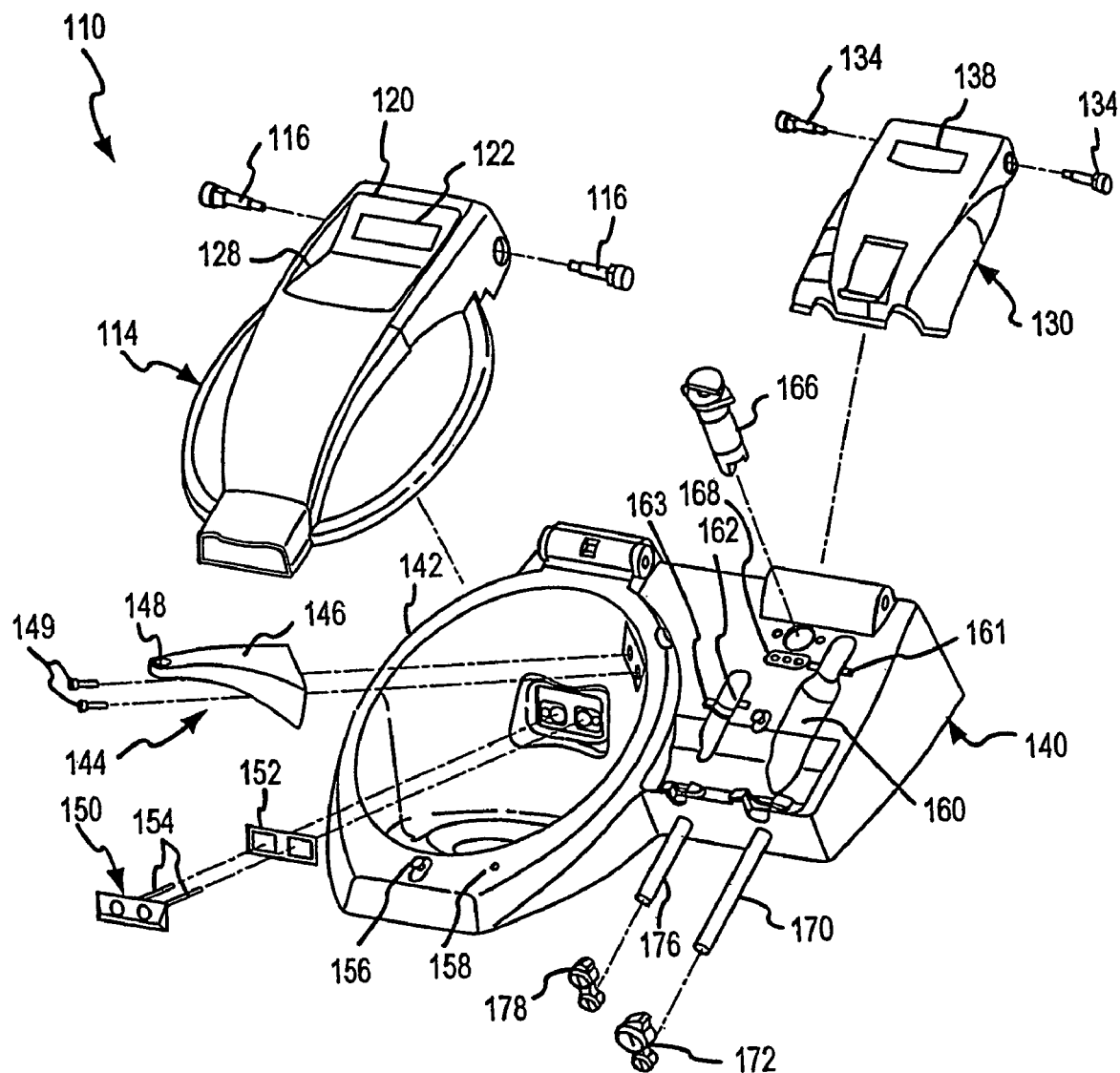
FIG. 3 is an upper perspective view of a disassembled upper housing assembly of one embodiment of a separation and collection system according to the present invention showing recesses for receiving and positioning a fill syringe and a withdraw or collection syringe and a centrifuge basin in which a positioning arm is used to support and position a tubing run of a disposable used in the system.

FIG. 3 illustrates an upper housing assembly 140 portion of the system 110. The upper housing assembly 140 includes a centrifuge cover assembly 114 typically formed at least partially of transparent or translucent plastic or other materials to allow processing operations to be observed by an operator. The centrifuge cover assembly 114 is mounted with pins or fasteners 116 to the upper housing 140 to allow opening of the cover assembly 114 for insertion and removal of a separation chamber and other portions of a disposable (e.g., tubing and a tube clamp). A cover latch 156 is provided to secure the cover assembly 114 in a closed position for operations and in some embodiments, the cover latch 156 includes a sensor for sensing when the cover assembly 114 is properly closes and to transmit a signal to a control system which responds appropriately with an error or prompt message (to close the cover 114) or with lighting of an indicator or LED 158 to indicate the cover 114 is closed. The cover assembly 114 further includes a user interface portion 120 for providing information to the operator including operating status, error messages, and input prompts and for receiving operator input including PRP collection volume and PPP collection commands. In one embodiment, the user interface portion 120 includes a display (with or without progress LEDs) for displaying text messages and a keypad for accepting operator input (such as "START" and "STOP" buttons, a PPP button, and incremental buttons for adjusting PRP collection volume).

The cover assembly 114 provides access to a centrifuge basin 142 in which a centrifuge is later installed and in which the operator positions a separation chamber and portions of tubing of a disposable on the chamber caddy with the tubing running through the centrifuge and out of the basin 142 to adjacent fill and withdraw syringes. As discussed above, the system 110 is configured for detecting a RBC/PRP interface in the later installed separation chamber and in this regard, a fiber optic assembly 150 with fiber bundles 154 is mounted within the centrifuge basin 142 with a support frame 152. The fiber optic assembly 150 is positioned precisely within the basin 142 so as to transmit beams of light from one bundle 154 toward the center of the basin, i.e., to contact a light pipe on a detector assembly on the chamber caddy to pass through the retained chamber and any fluid therein. Any light passing through the fluid is received by another light pipe and transmitted back to the fiber optic assembly 150 and second bundle 154 where it is transmitted for processing within the system 110 (e.g., a signal corresponding to the strength of the energy of the received light is transmitted to the control system for processing as discussed with reference to FIG. 2 in interface or level detecting in process 80). The fiber optic assembly 150 can include lenses that can be placed on the ends of the fiber optic bundles 154 to focus the light or energy onto the light pipes or from the light pipes (see FIG. 8 and corresponding text for the light pipes 332 of the detection assemblies 324, 328 on the caddy 214).

A positioning arm assembly 144 is provided to support a portion of the disposable tubing within the basin 142 and, importantly, to position the tubing in a desired location relative to the centrifuge. In one embodiment, the assembly 144 includes an arm 146 that is mounted with fasteners 149 to the basin 142. The arm 146 is designed to extend outward over the centrifuge to enable it to position a vertical run of the disposable tubing (e.g., tubing between the centrifuge and the arm 146) such that the longitudinal axis of the vertical tubing is substantially coaxial with the central axis of the centrifuge while allowing the tubing exiting the centrifuge to bow outward in an arc for ease of rotation (with the arc extending from the tip of the arm 146 to the exit aperture of the centrifuge). A releasable tube latch 148 is provided in the arm 146 to allow an operator to position the tubing (and more particularly, a tube clamp) within the latch 148 and then allow the latch 148 to close over or engage the tube clamp (as is explained in more detail with reference to FIGS. 9 and 11).

A syringe cover assembly 130 is mounted in the upper housing assembly 140 with pins or fasteners 134 to allow an operator to open the cover assembly 130 to insert and remove fill and withdraw syringes and to position and connect fill and withdraw lines of the disposable (not shown in FIG. 3). The cover assembly 130 is shaped with recesses to allow syringe plungers to extend outward from the upper housing assembly 140 to have the ends of the plungers engaged with knobs or pushers 172, 178 of syringe pumps (not shown) that are connected or driven by syringe pump shafts 170, 176. A transparent or translucent window 138 is provided in the cover assembly 130 to allow an operator to view a portion of the user interface of the system, i.e., the syringe display 168 that is used to indicate the presence and proper insertion of syringes and to indicate whether the cover assembly 180 is closed or open (which is sensed by detectors that transmit a signal to the control system of the separation and collection system 110). The upper housing assembly 140 includes an isolation valve (or pinch valve) 166 that is connected to tubing connected to a fill syringe (upstream of a Y-connector that connects both the fill and withdraw syringe to a single tube for connection to the separation chamber as shown in FIG. 1). The fill syringe, in some embodiments a 60 cc syringe, is installed in the housing assembly 140 in a fill syringe recess 160 which includes a syringe detector 161 for sensing the presence of the fill syringe and providing a corresponding signal to the control system. Similarly, the withdraw or collection syringe is loaded into the system 110 by placing it into withdraw syringe recess 162 which also includes a syringe detector 163 for sensing the presence of the syringe in the recess 162.

Figure 4:
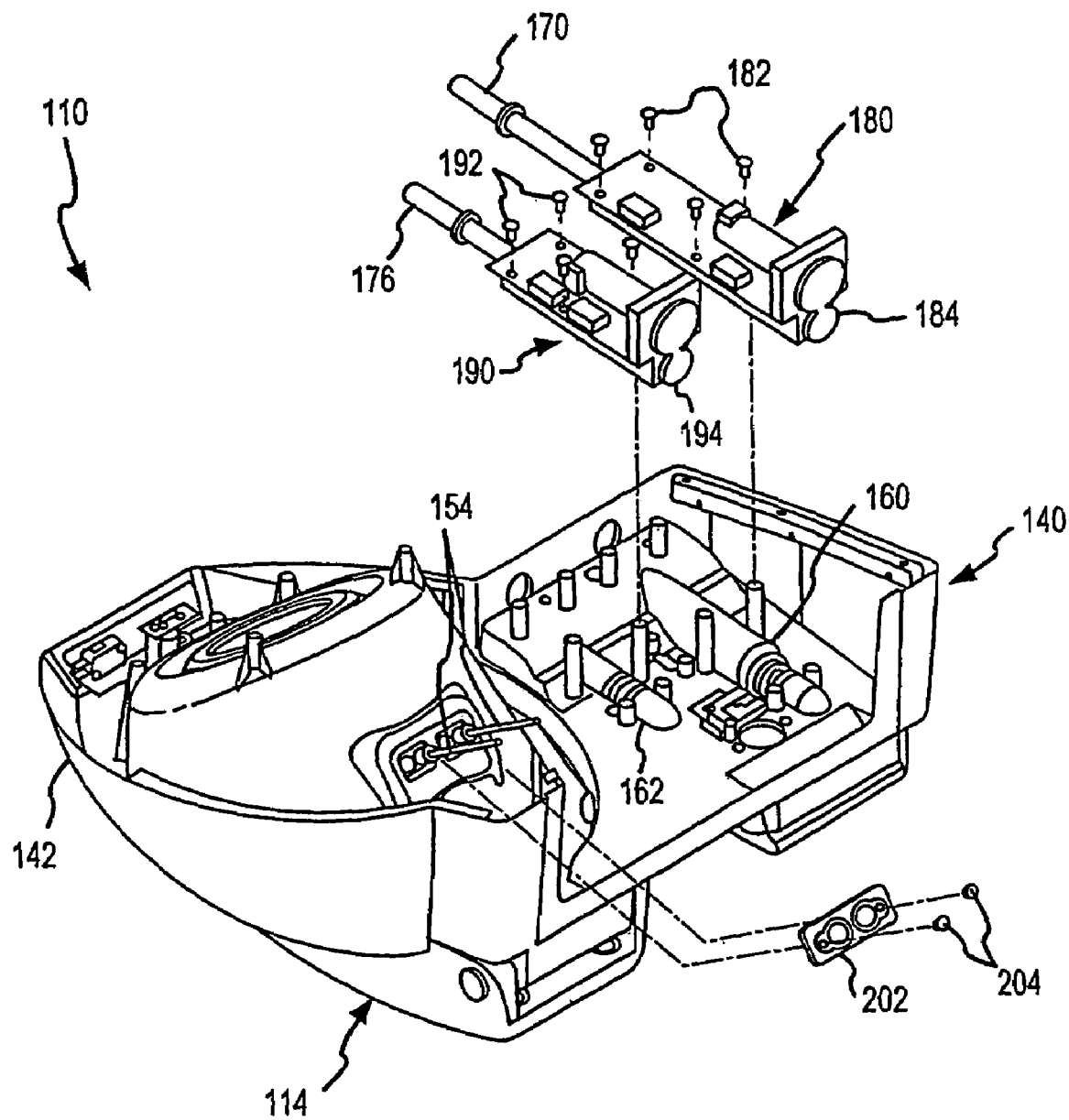
FIG. 4 is a lower perspective view of the upper housing assembly of FIG. 3 showing the mounting of two pumps for use in automated operation of the fill and collection syringes positioned in the recessed surfaces in the upper housing assembly shown in FIG. 3.

FIG. 4 provides a bottom view of the upper housing assembly 140 of the system 110. As shown, the fiber optic bundles 154 have been installed and extend outward from the basin 142 for connection to additional components of an interface detector (such as detector 62) and are further braced with mounting frame 202 and fasteners 204. FIG. 4 also illustrates the mounting of a fill pump 180 (e.g., a syringe pump) and a withdraw or collection pump 190 on the upper housing assembly 140 with fasteners 182 and 192, respectively. The pumps 180, 190 are positioned adjacent the syringe recesses 160, 162 to allow ready engagement of the drive portions of the pumps 180, 190 with plungers of syringes placed in the recesses 160, 162. Each pump 180, 190 includes motor-driven drive gears 184, 194 (shown covered in FIG. 4) for accurately and selectively moving the shafts 170, 176 (that are connected to knobs or pushers that mate with the plunger ends) inboard and outboard of the housing assembly 140 to move the plungers in and out of the syringes to force out or draw in known volumes of liquid.

Figure 5:
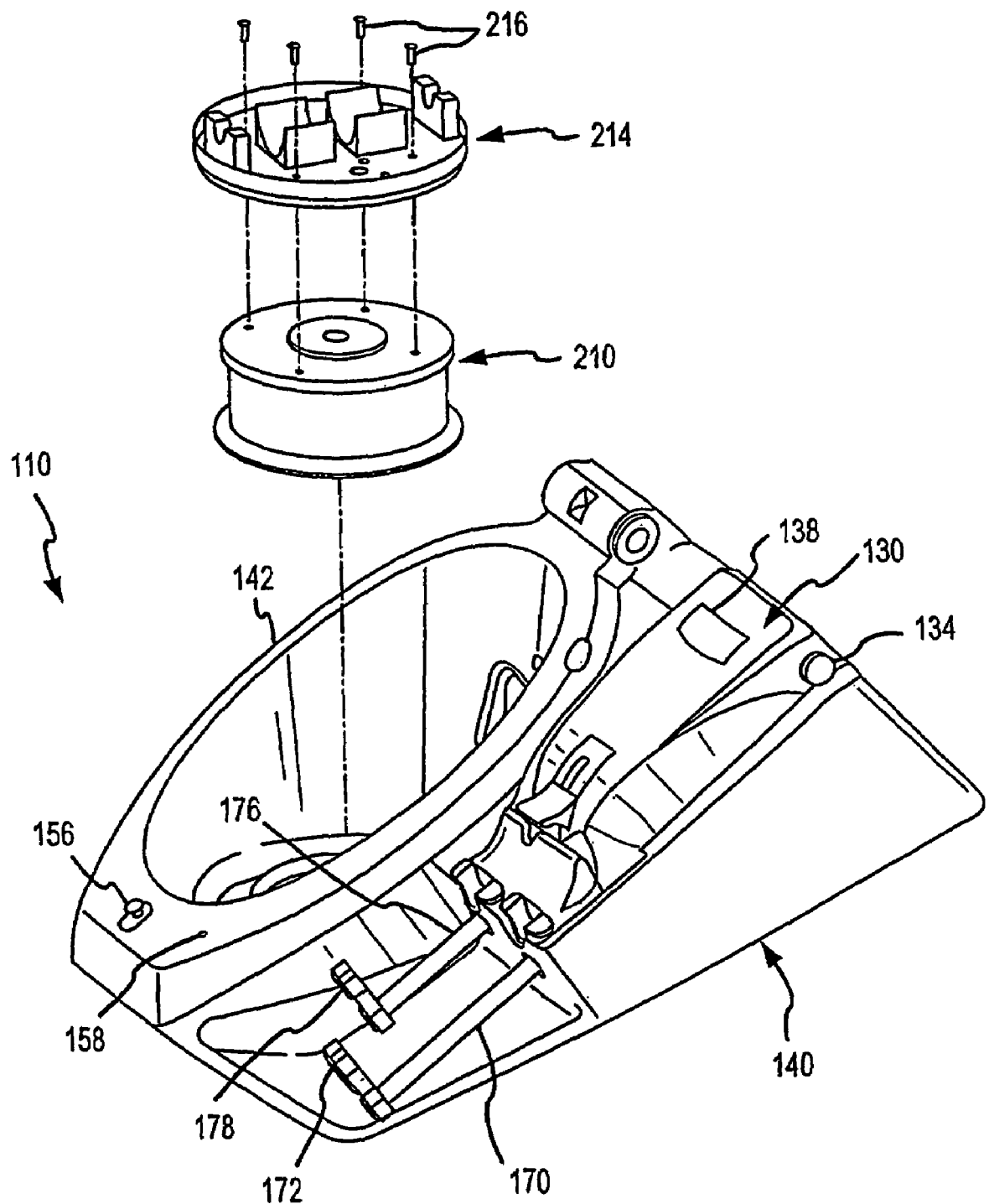
FIG. 5 is another perspective view of the upper housing assembly of FIG. 3 shown with the syringe cover closed and showing the positioning of a centrifuge within the centrifuge basin and the mounting of a caddy, for securely retaining and accurately positioning a disposable separation chamber, onto the upper cover or top plate of the centrifuge.

FIG. 5 illustrates additional assembly of the system 110 showing the upper housing assembly 140 with the syringe cover assembly 130 in a closed position with the centrifuge cover assembly 114 removed, and before installation of the arm assembly 144. A centrifuge 210 of the system 110 is shown prior to insertion in the basin 142 (and mounting to a drive). A chamber caddy 214 used to support a separation chamber and a portion of the disposable tubing during processing is mounted with fasteners 216 onto the top of the centrifuge 210. As will be explained further, the caddy 214 is configured to rigidly hold the chamber and to align portions of the chamber relative to the interface detector (such as the detector 62 of FIG. 1).

Figure 6:
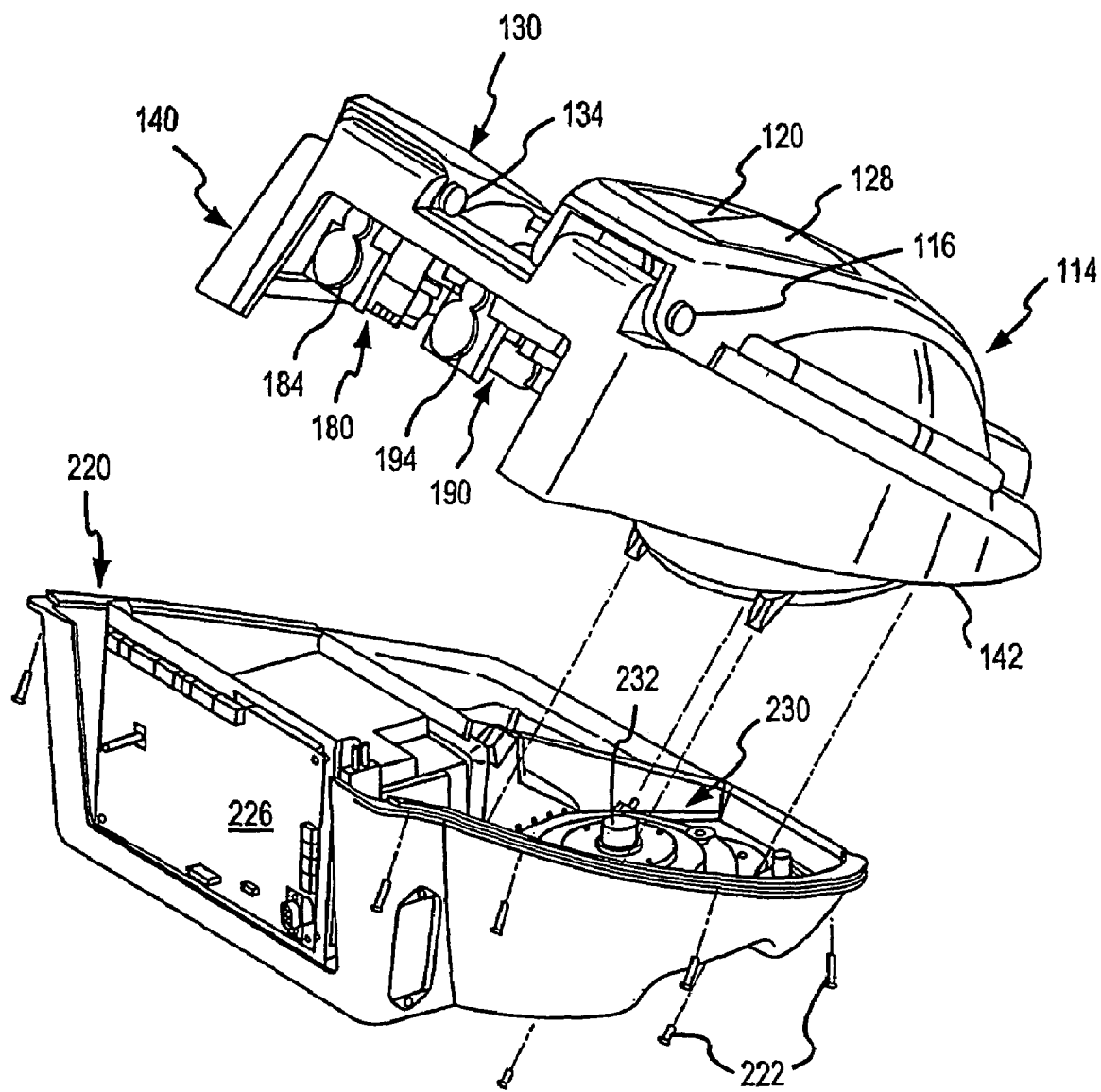
FIG. 6 is a rear perspective view of the separation and collection system showing the mounting of the upper housing assembly to a lower housing assembly that houses a controller system, a drive for the centrifuge, and power and communication components.

FIG. 6 illustrates further assembly of the system 110 with the mounting of the upper housing assembly 140 with fasteners 222 onto lower housing assembly 220. FIG. 6 shows the syringe pumps 180, 190 mounted onto the upper housing assembly 140 and covers 114, 130 in closed positions. The system 110 includes a drive assembly 230 with a square-type drive shaft 232 upon which the centrifuge 210 shown in FIG. 5 is mounted. Numerous drive types may be used to practice the invention if selected to provide the desired rotation speeds discussed as part of the separation and collection method 80 and to be controlled by an operations module. Preferably, the drive assembly 230 is selected to be quiet in operation with relatively low vibration, and may utilize pancake component gear sets to achieve high ratio precision speed reductions (e.g., support preferred slew rates) in compact or low profile packages. A controller 226 with circuitry and other hardware (such as microprocessors, memory, and the like) to provide the functions of control system 12 of FIG. 1. As such, the controller 226 is connected to the drive assembly 230, to the pumps 180, 190, and to various sensors (including interface detector components) within the system 110 upon installation and assembly of the system 110.

Figure 7:
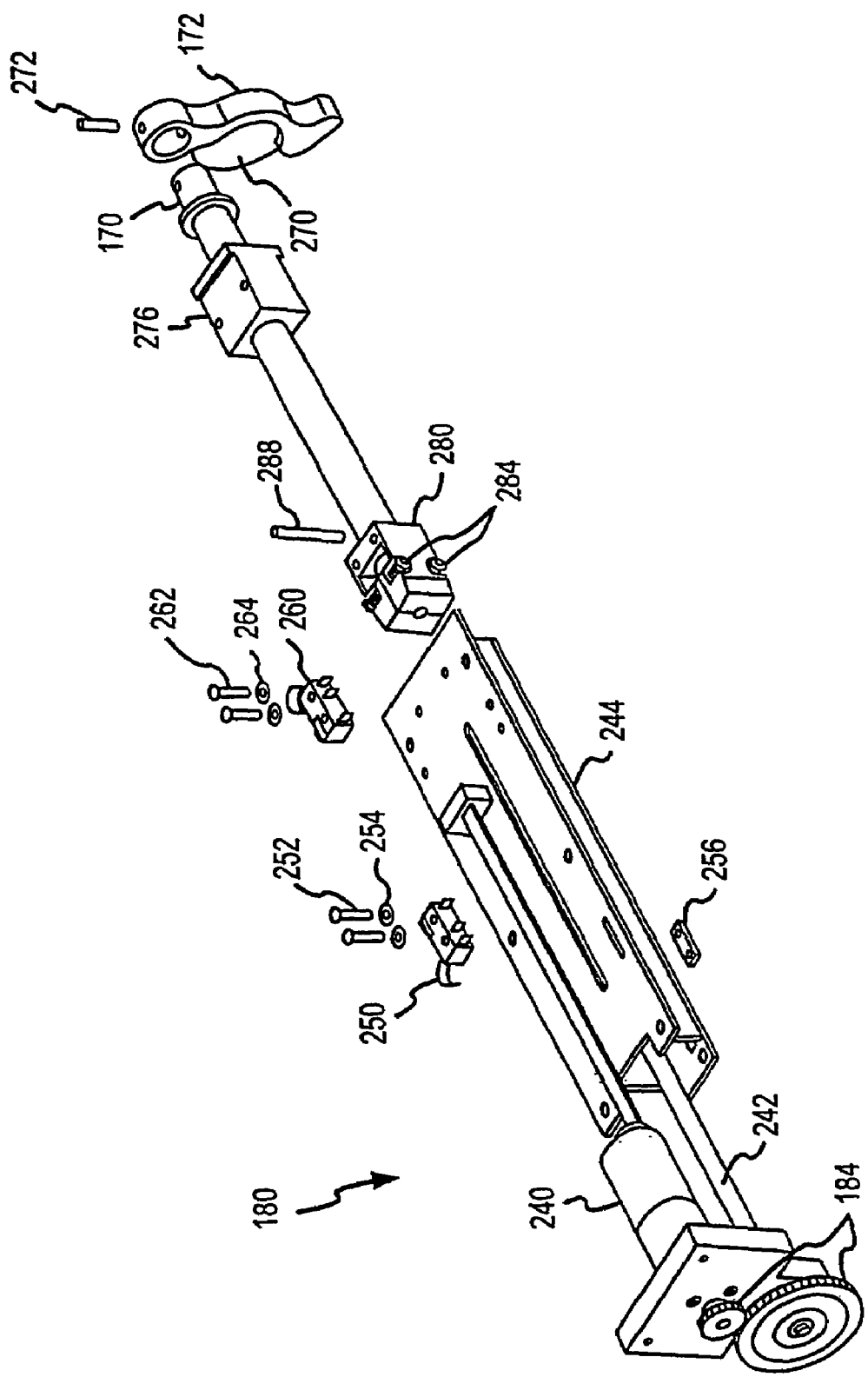
FIG. 7 is an exploded view of a syringe pump used shown being installed in FIG. 4 illustrating a handle or pusher with a recessed surface for receiving a syringe plunger end, a self-engaging drive nut controllable with the handle for engaging a drive shaft or screw, and a pair of limiting switches for controlling travel of the drive screw.

FIG. 7 illustrates the fill pump 180 in more detail to illustrate the components that allow the pump 180 to be engaged with a plunger end of a syringe and to automatically reconnect or re-engage the drive components (with the collection pump 190 being similar in configuration but typically adapted for a smaller syringe). As illustrated, the pump 180 includes two drive gears 184 selected to achieve a desired gear ratio for moving an engaged syringe plunger at a known rate (useful for pumping processes where rates are important such as described for process 80 of FIG. 2). One gear 184 is attached to a drive motor 240 that is rigidly mounted to a pump housing 244. The other drive gear 184 is attached to the drive screw 242 which extends inward into the housing 244.

An important aspect of the pump 180 is that in practice an operator is able to readily engage an end of a plunger during loading (with the plunger extended for a full syringe and inserted for an empty or partially empty syringe) and to easily disengage the plunger from the pump 180 to remove the syringe from the system 110. To achieve these functions but yet provide desired drive features, the pump 180 includes a shaft 170 upon which a pusher or knob 172 is mounted with set screw 272. The knob 172 includes a planar recessed surface 270 for mating with the relatively flat outer surface of a syringe plunger. A bushing guide 276 is also mounted on the shaft 170 and at the other end of the shaft 170 from the know 172 is a drive nut 280. The drive nut 280 (such as a cam-type drive nut) is mounted or secured with dowel pin 288. In operation, the drive nut 280 is held onto the drive screw 242 and engages the drive screw 242 by the force of the springs 284. When an operator rotates the knob 172 (such as 90 degrees), the internal configuration of the drive nut 280 (e.g., cams) force the springs 284 to compress and opens the end of the nut 280 to disengage the nut 280 from the drive screw 242. When disengaged, the syringe is inserted in the recess (160 of FIG. 3) with the plunger extending outward from the upper housing assembly 140 and the knob 172 can be pulled or pushed as necessary to move the shaft 170 and drive nut 284 so as to align the surface 270 with the plunger end. When relatively aligned, the knob 172 is released which due to the expansion of the springs 284 and internal cam action of the drive nut 280 results in the shaft 170 rotating along with the knob 172 such that the surface 270 engages the plunger end and the drive nut 280 engages the drive screw 242 at the present location of the drive nut 280. In some embodiments, the drive nut 280 is not spring loaded and an operator would manually turn the knob 172 to re-engage the drive nut 280 and drive screw 242. To allow the two end positions of travel for the knob 172 (and attached plunger end) to be detected, the pump 180 includes two switches 250, 260 that are mounted to the pump housing 244 with fasteners 252, 254, 256, 262, 264 and are positioned at spaced apart locations selected such that the switches contact a portion of the drive nut 280 or other portion of the shaft 170 to detect when a plunger attached to the knob 172 would be fully extended and fully inserted. The switches 250, 260 being adapted to transmit a signal to the controller 226 (shown in FIG. 6) when engaged or contacting the drive nut 280 or other portion of the shaft 170 which is processed as end-of-travel signals for controlling operation of the system 110.

Figure 8:
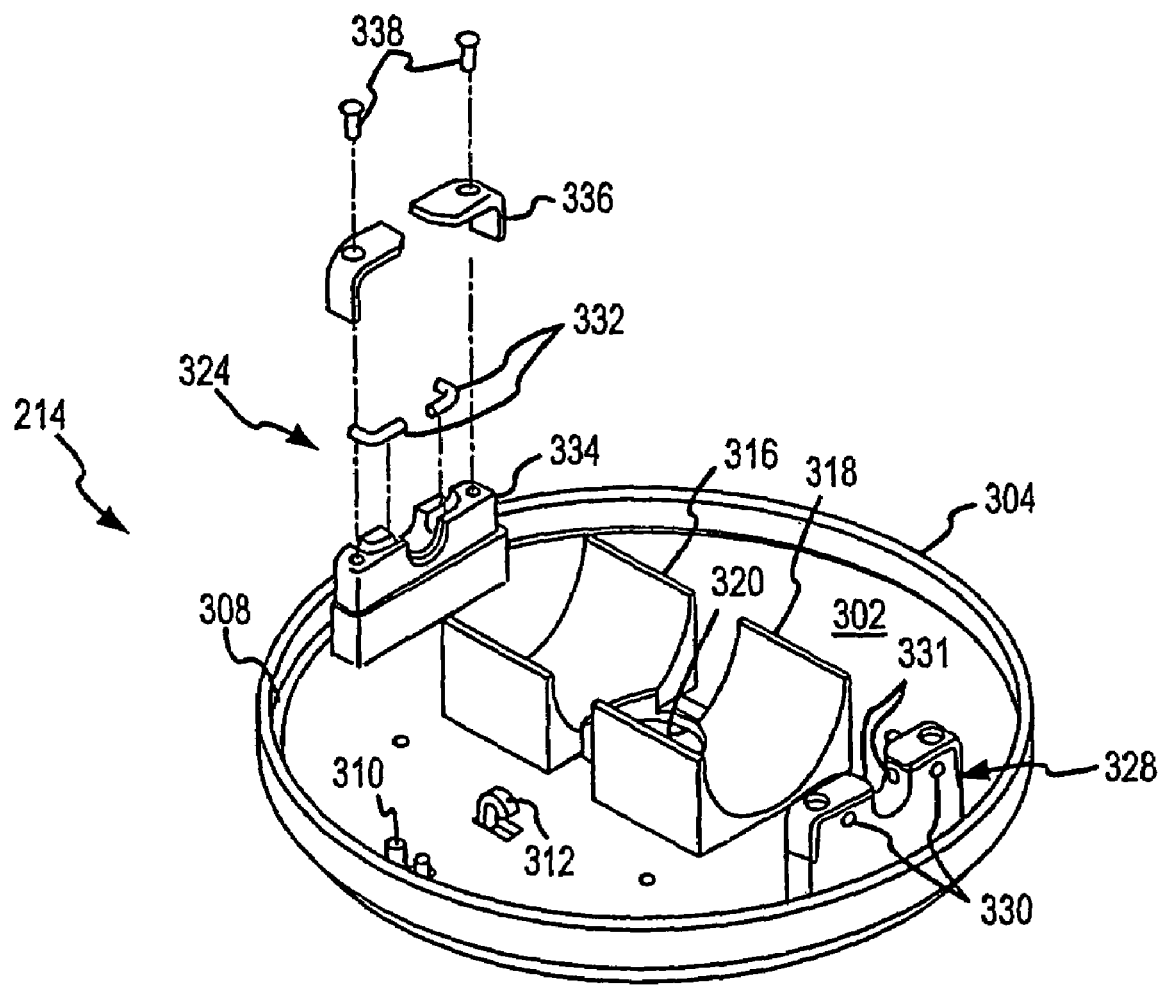
FIG. 8 illustrates in more detail the caddy shown in FIG. 5 illustrating the positioning of light pipes in level detection assemblies that are also used to physically support and position inlet/outlet ports of a separation chamber, i.e., nipples adjacent the light pipes to facilitate detection of interfaces between separated components or fractions.

Referring to FIG. 8, the chamber caddy 214 shown mounted to the top of the centrifuge 210 in FIG. 5 is shown in more detail. As discussed previously, the system 110 is designed for low centrifuge rotation and separation and as such, preferably is very well balanced. The caddy 214 is configured to provide weight balancing by providing symmetric aspects as well as weight reduction aspects useful for balancing after loading of the disposable (chamber and tubing). The caddy 214 is also configured for rigidly supporting the chamber and tubing and for aligning the chamber with interface detection components. As illustrated, the caddy 214 includes a base 302 with a side wall 304 and with a tube trough or recessed surface 308 on approximately one half of the perimeter of the base 302. As will become clear, the tubing of the disposable is shaped in an arc (see FIG. 9) that coincides with the shape and size of the trough 308. The trough 308 acts to position and support the tubing of the disposable on the base 302 and also the removal of material from the base 302 for the trough 308 acts to assist in balancing the caddy 214 for enhanced rotation characteristics with the weight of the tubing and fluid in the tubing in the trough 308 being at least partially counterbalanced by the material remaining in the base 302 at the base of the wall 304 on the opposite side of the base 302 from the trough 308. Ribs (not shown) may further be added underneath or on top of the half of the base 302 opposite the trough 308 to enhance balance of the caddy 214. Retaining elements 310, 312 are provided to restrain movement of the disposable tubing during rotation. Two saddles 316, 318 are provided to support the two halves of the chamber and are typically formed of a resilient material that is sized slightly smaller than the chamber halves to provide force-fit within the saddles 316, 318. A hole or aperture 320 is provided in the base 302 to provide a path for the disposable tubing underneath the chamber when the chamber is installed in the saddles 316, 318.

The caddy 214 further includes two level detection assemblies 324, 328 that are configured to position nipples of the chamber adjacent light detection devices and to align the light detection devices with the fiber optic assembly 150 shown in FIG. 1. The use of two detector assemblies 324, 328 is desirable for obtaining interface detection twice during each rotation of the caddy 214 but in some embodiments, the detection portions of one of the level detection assemblies 324 or 328 can be removed with that assembly 324 or 328 simply acting as a support for the chamber and as a counterbalance for the weight of the other assembly 324 or 328. As illustrated for assembly 324, two sections of light pipe 332 is inserted in a detection base 334 to provide a path for light transmitted from the fiber optic assembly 150 to travel and to direct the light through the nipple of the chamber and any fluid therein and then be redirected outward from the assembly 214 back to the fiber optic assembly 150. A cover 336 is placed over the light pipes 332 and attached with fasteners 338. Assembly 328 is assembled and shows the inlet and outlet 330 to and from the assembly 328 and the inlet and outlet 331 for light to travel through the chamber nipple positioned in the adjacent recesses portion of the assembly 328.

Figure 10:
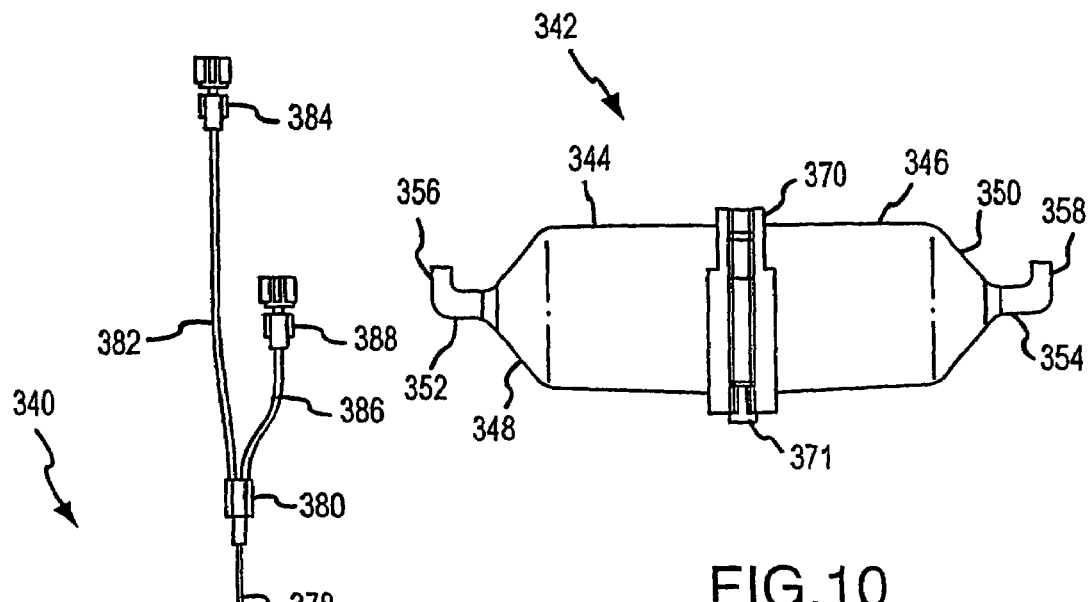
FIG. 10 is an enlarged view of the separation chamber of FIG. 9 illustrating that the chamber is a two part chamber separated by a vented cap configured to equalize and/or release gases by venting and to guide the tube of the disposable down into the upper opening of the centrifuge and illustrating the use of a single port for concurrent filling and withdrawing of fluids in each side of the chamber.
Figure 9:
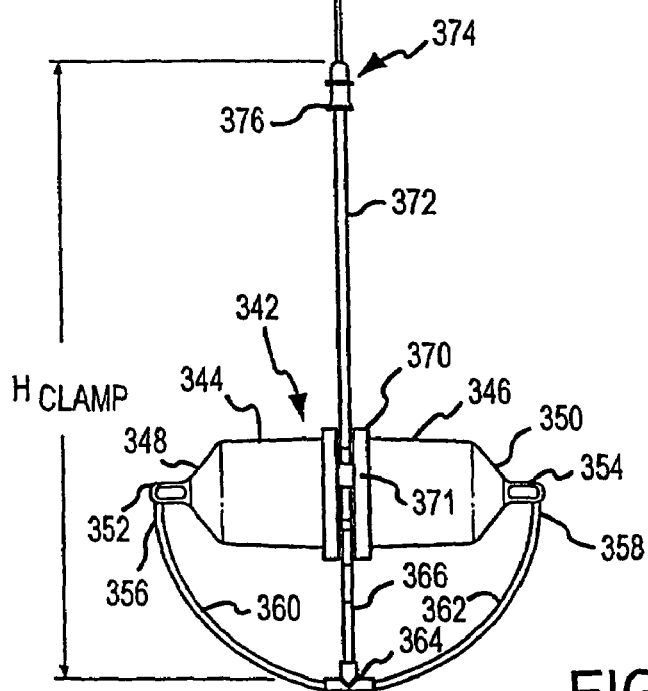
FIG. 9 shows one embodiment of a disposable assembly for use with the separation and collection system of FIGS. 3-6 including a separation chamber adapted for insertion on the caddy and tubing and tubing components useful for connection to the tube positioning arm, for flow control by the isolation valve, and for fluid connection to the fill and collection syringes.

FIGS. 9 and 10 illustrate the disposable 340 that is used within the system 110 that is installed along with fill and withdraw syringes at the start of each processing (such as processing 80) and then removed for disposal after the completion of the process. The disposable 340 includes the chamber 342 that is fabricated from a relatively transparent plastic or other material to allow light or other energy for interface detection to pass through its walls. The chamber 342 is configured for self-balancing and hence, is symmetric and divided into two halves or segments 344, 346. The segments 344, 346 are separated by a divider 370 that includes a vent 371 that is in communication with both segments 344, 346 to allow gas to be vented during fill and other processes. The divider 370 is shaped to allow the tube (between 366 and 372 in FIG. 9) to be guided beneath the divider 370 when installed and fed through the caddy aperture 320 (shown in FIG. 8). Each chamber segment 344, 346 further includes a sloped or reduced portion 348, 350 that tapers downward to concentrate the volume of separated materials having a smaller volume (such as PRP) to a much smaller diameter at the nipples 352, 354 to assist in RBC/PRP interface detection by light shown through the pipes 332 and nipples 352, 354 (and any liquid within the nipples 352, 354). In the illustrated embodiment, a single port 356, 358 is provided for inputting and withdrawing fluids and fluid components from the chamber segments 344, 346. The chamber 342 is installed onto the caddy 314 with the segments 344, 346 mating with saddles 316, 318 and the nipples 353, 354 positioned within upper recessed surfaces in the level detection assemblies 324, 328 adjacent inlet and outlet 331 of light pipes 332.

As shown in FIG. 9, the disposable 340 includes runs of tubing, such as single lumen plastic tubing (such as urethane tubing). At the chamber 342, tubing 360, 362 is connected to the ports 356, 358 and is connected together by connector 364 (e.g., a tubing tee) and another run of tube 366 is connected to the connector 364. When installed on the caddy 214, the runs of tubing 360, 362 are inserted at least partially into the trough 308 in the caddy base 302, the connector 364 is inserted in retainer 310, and the tubing run 366 is placed under retaining element 312. The tubing run 366 is passed into a guide surface of the chamber divider or cap 370 and is passed through the caddy aperture 320 and through the centrifuge (as will be discussed in more detail below). The tubing 372 of the disposable 340 is linked to the tubing 366 (or is the same tube section) and when installed exits an aperture in the side of the centrifuge and is drawn up vertically to a tube clamp 377 having a clamp taper or tapered section 376.

The tubing clamp 377 in one embodiment is a two part connector that when snapped together over ends of tubing 372, 378 reduces the diameter of the tubing 372, 378 by applying a load or inward force around the circumference of the tubing ends. This clamping force controls tube sliding (axially or rotationally) while the loop formed in the tubing 372 is rotated by the centrifuge 210. The height, $H_{CLAMP}$, of the tube clamp 374 is selected to allow the disposable 340 to be fit into the system 110 and to engage a support arm assembly 144 while still also providing enough slack to define a tubing arc external to the centrifuge to not contact the centrifuge. In one embodiment, the height, $H_{CLAMP}$, is about 16 inches but of course will vary with centrifuge design and positioning of the arm assembly 144 relative to the centrifuge (and for ease of measurement the height, $H_{CLAMP}$, is typically measured by measuring the length of the tubing 366, 372). The disposable 340 further includes a run of tubing 378 from the clamp 374 to a dividing connector 380 (e.g., a Y-type connector and see connector 49 of FIG. 1). The disposable 340 then branches to a fill line 382 with a syringe connector 384 and a collection or withdraw line 386 with a syringe connector 388 to allow these two branches of the disposable 340 to be readily connected to fill and collection syringes, respectively.

Figure 11:
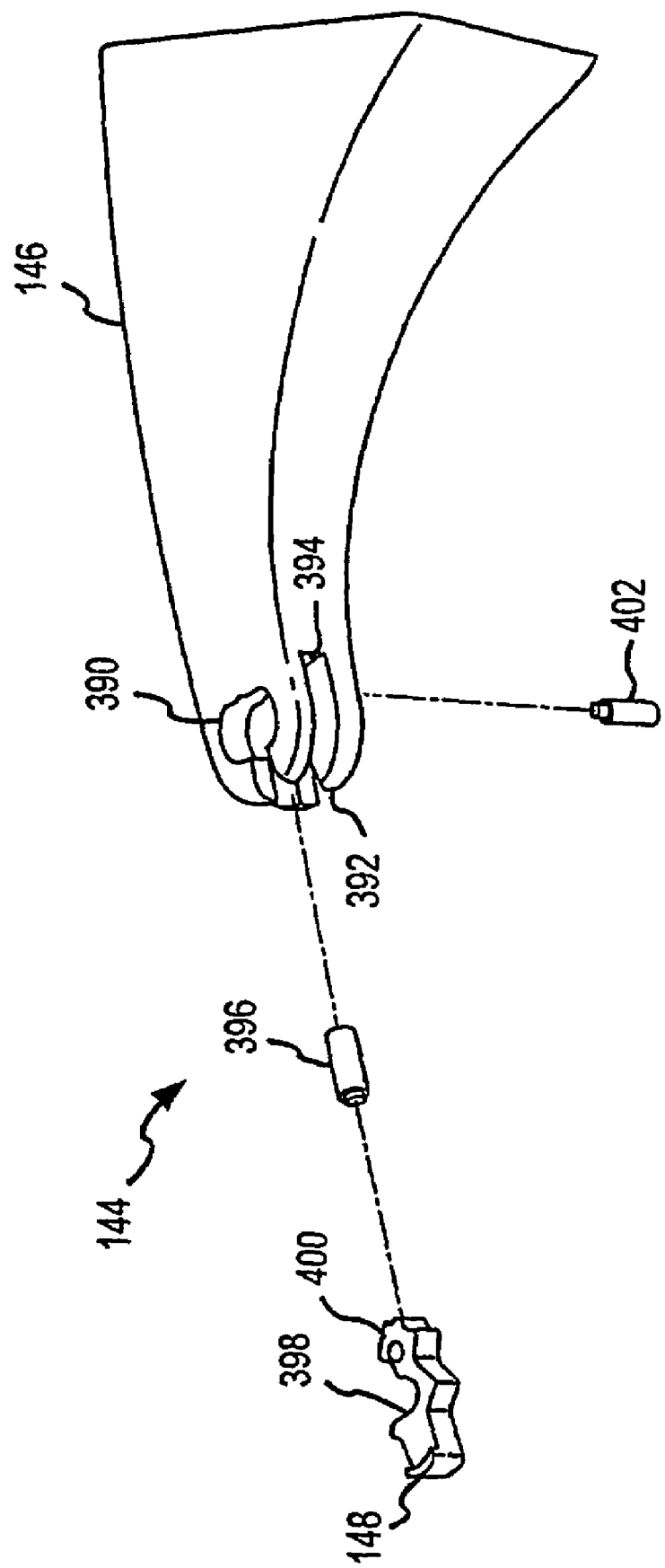
FIG. 11 is an enlarged view of the tube positioning arm of FIG. 3 better showing the tube latch that is rotatable through a horizontal groove in the arm tip to allow positioning of a tube (and more specifically, a tube clamp) within the arm and that is adapted to return to its original position to latch onto the tube clamp to retain and position the tube of the disposable in a desired position relative to the centrifuge.

FIG. 11 illustrates in more detail the arm positioning assembly 144 that is used in practice to support the disposable 340 by connecting to the tube clamp 374. The arm positioning assembly 144 includes an arm 146 and a latch 148. The latch 148 includes a clamp mating surface 398 and a hole 400 for pivotally mounting with pin 402 to the arm 146. The arm 146 includes a tube aperture 390 for allowing the tube 372, 378 to enter the arm 146 and a front aperture 392 for receiving the tube clamp 374. A side or horizontal latch groove 394 is provided to allow the latch to be rotated about pin 402. A ball plunger 396 is provided is used such that when an operator rotates the latch and inserts the tube clamp 374 the operator can release the latch 148 and the plunger 396 automatically forces the latch 148 at surface 398 to contact and mate with the tube clamp 374 just above a clamp taper 376 on the tube clamp 374. In one preferred embodiment of the method 80 or for general practice, the taper 376 is lubricated, such as with silicon oil, to reduce frictional forces which can cause heat build up in the tube clamp 374, binding, or other operational difficulties. Alternatively, the lubrication to reduce friction is provided on the skid plate 440 on at least a portion of the contact surfaces or incorporated in the material(s) used to fabricate the skid plate 440 or at least to manufacture contact surfaces of the skid plate 440.

In practice, operation of the system 110 is enhanced by lubricating of the disposable 340 tubing at mating points between rotating parts of the disposable 340 and the other components of the system 110. These points are at the tube clamp 374 and below (or towards the centrifuge 210). The lubricant may be a silicone-based lubricant or other lubricant that is compatible with the material of the disposable 340 components and the materials of the mating components (which are typically formed of some type of plastic). The lubricant can be applied to the contact points of the disposable 340 such as at the clamp 374 and taper 376 which mates with the latch 148 of the arm assembly 144, and portions of the tubing 372, 366 that will contact the skid plate 440 and other internal portions of the centrifuge 210 on the tube path 490 or alternatively, all of the disposable 340 from the tube clamp 374 down to about the connector 364 can be lubricated or a surface treatment can be used on these disposable 340 components.

FIGS. 12-22 are provided to illustrate fully the details of one preferred embodiment of the centrifuge 210 although the process 80 of FIG. 2 can be implemented with differing centrifuge configurations. The centrifuge 210 is adapted to mate with the square drive shaft 232 of drive assembly 230 that provides an input rotation speed which is doubled by the centrifuge 210 for a 2:1 input to output ratio. Additionally, the centrifuge 210 utilizes a unique two-belt arrangement such that the top plate 410 that is rigidly attached to the chamber caddy 214 is rotated in the same direction as components within the centrifuge 210 that rotate at half the speed (e.g., the top plate 410 rotates twice as fast but in the same direction as other centrifuge components, such as the shield 414 with window 416). The use of bearings, use of small pulleys, and arrangement of components within the centrifuge 210 leads to a very compact centrifuge with no external belts or gears that runs quietly with little vibration which is very useful to maintain alignment of the caddy 214 and retained chamber 342 with level detection portions of the system and reduces movement of the RBC/PRP interface and movement of separated components among adjacent fractions, thereby enhancing collection of PRP. Importantly, a tube path 490 is provided through the centrifuge 210 that maintains a desired shape of the disposable tubing for fluid flow and controls tubing twisting and binding and reduces coefficient friction to limit heat buildup and wear to the tubing that may cause tubing failure. While these features of the centrifuge 210 have been combined to provide a significantly improved centrifuge 210, it will be apparent to those skilled in the art that some or all of these features can be practiced separately, e.g., the creation of a tube path with a shape that reduces wear and binding would be useful in centrifuges with different gearing, belts, and drive configurations that centrifuge 210.

Figure 12:
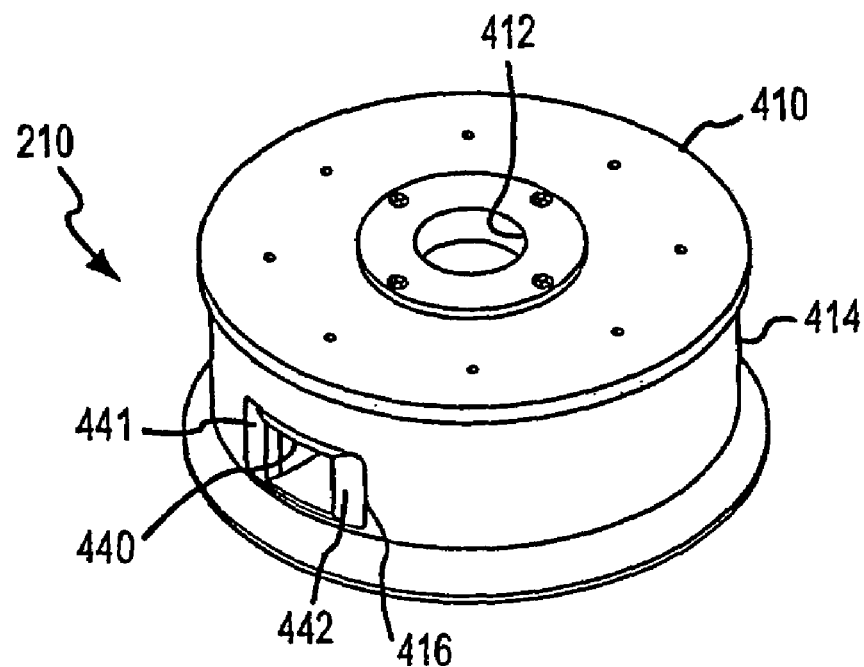
FIG. 12 is an enlarged perspective view of the centrifuge of FIG. 5 illustrating more clearly an upper opening or aperture and a side window through which the tubing of the disposable assembly is passed prior to separation and collection processes.

Referring first to FIG. 12, a centrifuge 210 is illustrated that includes a top plate or cover 410 upon which the caddy 214 is rigidly mounted to be rotated with the plate 410. The top plate 410 includes an aperture 412 through which the tubing of the disposable 340 is passed upon initial installation of the disposable 340 in the system 110 and remains during processing (such as tubing run 366, 372 shown in FIG. 9). The centrifuge 210 includes an outer shield or sidewall 414. The shield 414 includes a window or opening 416 through which the tubing of the disposable 340 is passed upon installation and remains during processing (tubing run 372 shown in FIG. 9). As will be explained in more detail, a skid plate 440 and side plates 441, 442 are provided to define the tube path (see path 490 in FIG. 19) and defines the contact and wear surfaces for the tubing, e.g. tubing 372, when the sidewall 414 rotates.

Figure 13:
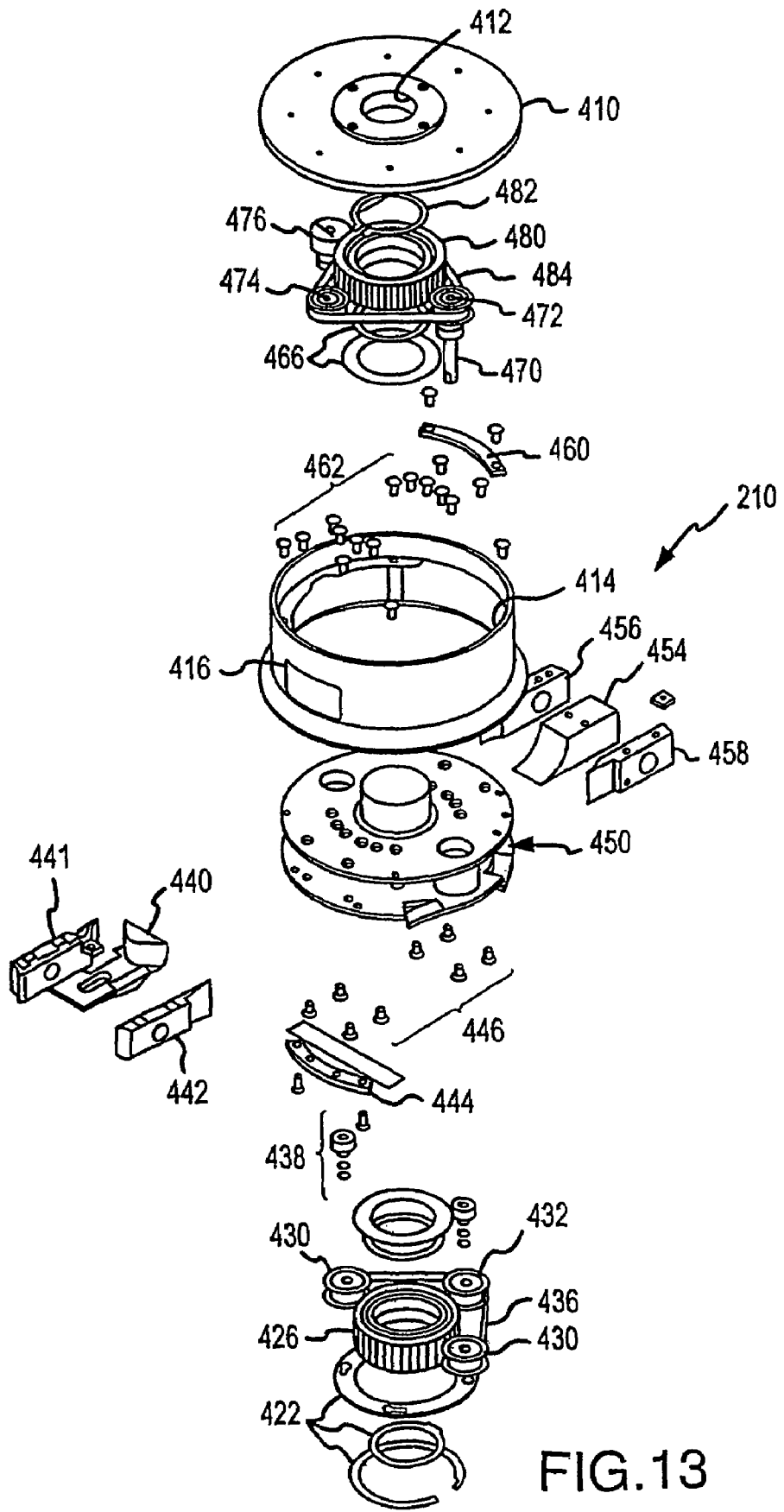
FIG. 13 is an exploded perspective view of the centrifuge of FIG. 12 showing the inclusion of an upper and a lower drive belt each with different installation arrangements to provide a desired rotation of the centrifuge and showing the use of a diverter and skid plate to create a tube path through the centrifuge between the upper opening and the side window with curved surfaces for improving guiding the tubing of the disposable through the centrifuge and providing a desirable contact surface for the tubing during centrifuge rotation to reduce wear and binding of the tube.

FIG. 13 is an exploded view of the centrifuge 210. The centrifuge 210 includes retaining rings 422 and a lower, fixed or stationary pulley 426 with outer teeth. Adjacent the pulley 426 are two satellite pulleys 430 and a tensioner 432. According to a significant aspect of the centrifuge 210 is the use of a double-sided drive belt 436 that mates with the satellite pulleys 430 and tensioner 432 with a first side of the belt 436 and with the teeth of the pulley 426 with a second side of the belt 436. The lower pulley assembly mates with a drive core assembly 450 with the use of bearings and spacing discs 438. The drive core assembly 450 is balanced (if appropriate) with a balancing weight 444.

To create a tube path in the centrifuge 210 and through the drive core assembly 450, the skid plate 440 with side plates 441, 442 are mounted within the drive core assembly 450 with fasteners 446, 462. Additionally, diverter 454 with side plates 456, 458 are mounted in the drive core assembly 450 with fasteners 446, 462 to provide a lower curve or elbow the tube path to redirect the tubing with a desirable rounded bend (rather than a sharp corner that could pinch flow or cause undesired wear) through the window 416. The drive core assembly 450 is encased in the shield 414 which is rigidly fastened with fasteners 462 to the drive core assembly 450 and the centrifuge 210 is further balanced (if necessary) with upper balancing weight 460.

An upper drive assembly is mounted on the drive core assembly 450 with disks or spacers 466 and a top pulley 480 is slid over the center core of the drive core assembly 450. A shaft 470 and satellite pulley 472 along with a tensioner 474 are positioned adjacent the pulley 480 along with a spinner 476. A single-sided belt 484 is placed in contact with the pulley 480, the satellite pulley 472, and the tensioner 474. A retaining ring 482 is provided and the top plate 410 is positioned over the top pulley to rest within the shield 414 but is rigidly mounted to the top pulley 480 to rotate with the pulley 480, i.e., twice as fast but in the same direction as the core assembly 450.

Figure 15:
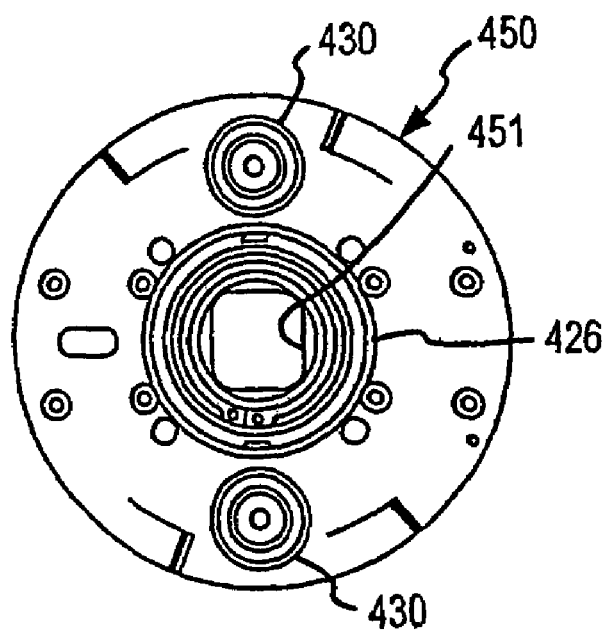
FIG. 15 is a bottom view of the assembled subassembly of FIG. 14 showing the use in one embodiment of a square drive for the centrifuge.
Figure 14:
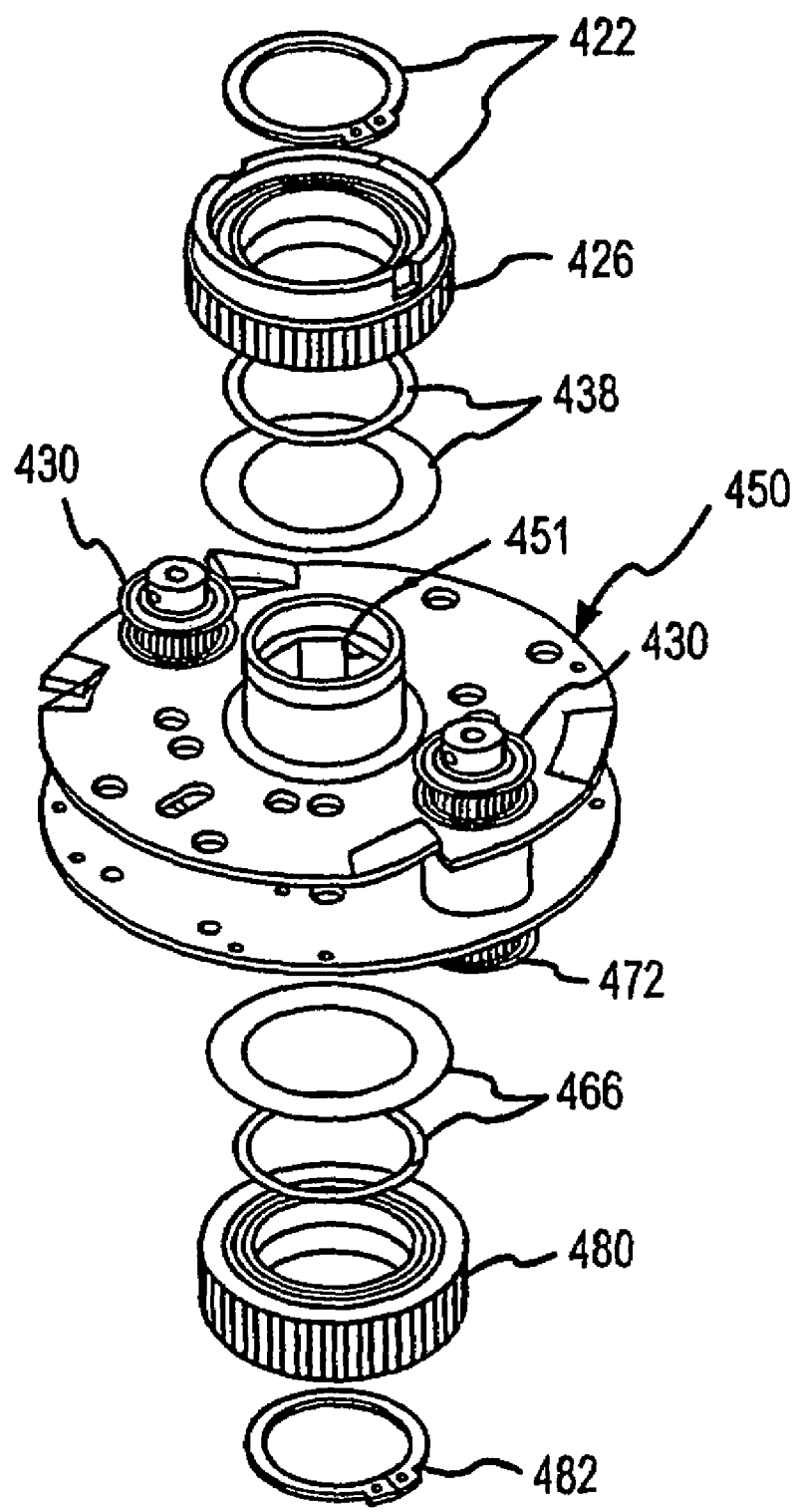
FIG. 14 is a partial exploded view similar to FIG. 13 illustrating a drive subassembly of the centrifuge.

FIG. 14 provides another view of portions of the centrifuge 210 illustrating the lower portion of the drive core assembly 450. As shown, disks 438 are slid over the core of the assembly 450 along with the lower pulley 426 with is attached with rings 422. The satellite pulleys 430 are shown installed over bearings 438 (not visible in FIG. 14) and attached to the shaft 470 of upper pulley 472 and a shaft of the spinner 476 (not shown). The core drive assembly 450 has an inner square drive 451 for mating with the square of drive shaft 232 of drive 230. FIG. 14 further shows the disks 466 placed over the core of assembly 450 prior to placement of upper pulley 480 followed by split ring 482. FIG. 15 provides an additional view of the drive core assembly 450 after the installation of the pulley 426 and satellite pulleys 430 prior to the installation of the tensioner 432 and belt 436. This view more clearly shows the inner square drive 451 of the core assembly 450.

Figure 16:
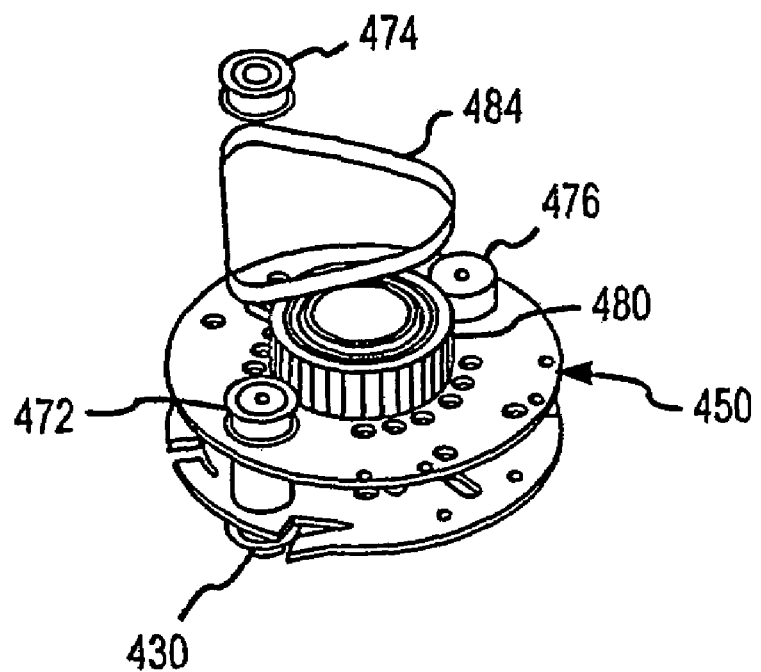
FIGS. 16 and 17 are partial exploded views of the drive subassembly of the centrifuge illustrating the use of a single-sided upper belt and a two-sided lower belt to drive the upper portion or cover of the centrifuge at a speed of twice the input speed and in a desired direction.
Figure 17:
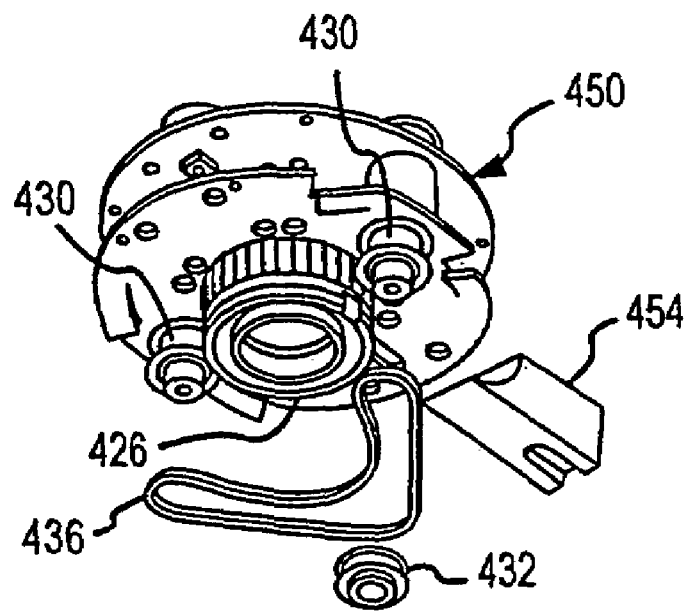

FIG. 16 illustrates further the combined use of a single-sided belt 484 to contact the upper pulley 480 which is attached to the upper plate 410. FIG. 17 shows the lower pulley 426 and associated satellite pulleys 430 and tensioner 432. The two-sided belt 436 is shown with its V-shape for contacting the pulleys 426, 430 and tensioner with both sides. FIG. 17 further shows the positioning of diverter 454 in core assembly 450.

Figure 18:
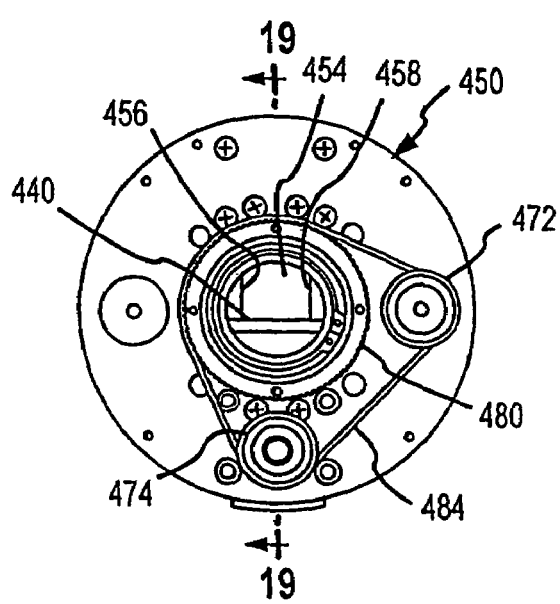
FIG. 18 is a top view of the drive subassembly with the top drive belt installed showing the placement of the belt on the exterior surfaces of the center gear, tensioning pulley, and drive gear.
Figure 19:
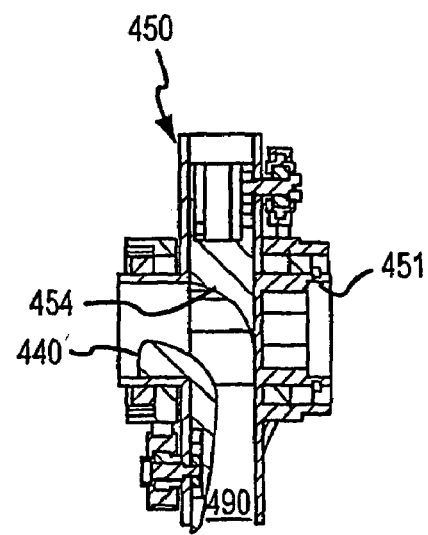
FIG. 19 is a sectional view taken at line 19-19 in FIG. 18 illustrating the unique tube path defined in the centrifuge by the combination of the diverter, the skid plate, and the side plates.

FIG. 18 provides a view looking down onto the core drive assembly 450 after installation of the upper pulley 480, tensioner 474, satellite pulley 472, and one-sided belt 484 but without showing the side shield 414 or top plate 410. FIG. 19 also shows the inner square drive 451 for mating with the drive shaft 232 of the drive assembly 230. The diverter 454 and corresponding side plates 456, 458 along with the skid plate 440 are shown installed within the core drive assembly 450, with the surface of 454 redirecting installed tubing through the core drive assembly 450. FIG. 19 is a sectional view of the portion of the centrifuge 210 shown in FIG. 18. As shown, the core drive assembly 450 is shown with the diverter 454 and skid plate 440 that include surfaces which define the centrifuge tube path 490 (i.e., through the top plate aperture 412 in the top plate 410, through the top portion of the core of the assembly 450, and out the window 416 in the shield 414.

The shape of the tube path 490 (and, hence, the shape of the skid plate 440 and diverter 454) is selected to provide for easy installation of the tubing of the disposable 340. Significantly, the tube path 490 defined by the skid plate 440 and diverter 454 helps to define or form the disposable tubing into a loop that rides on the skid plate 440 during rotation of the centrifuge 210 and controls twisting, binding, and failing of the formed loop in the disposable 340. The skid plate 440, and typically the diverter 454 and side plates 441, 442, 456, 458, are formed with smooth surfaces formed of delrin plastic or other material that has a low coefficient of friction to minimize wear and heat build up but that is relatively tough or wear resistant to provide a longer operational life for these centrifuge components. The skid plate 440, and typically the diverter 454 and side plates 441, 442, 456, 458, in some embodiments, include vent holes formed by the combination of the components or integral to these components that facilitate heat removal from these components and particularly the skid plate 440 by air flow to maintain a lower or acceptable skid plate and other contact surface temperature.

Figure 20:
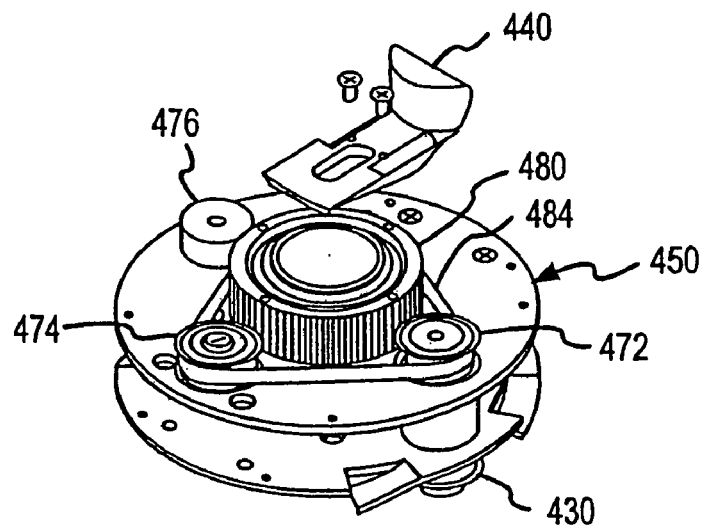
FIGS. 20-22 are additional perspective views of the centrifuge showing insertion of the skid plate, skid plate side plates, and the shield with a path through the shield window being defined by the side plates and skid plate (as well as other portions of the drive subassembly.
Figure 21:
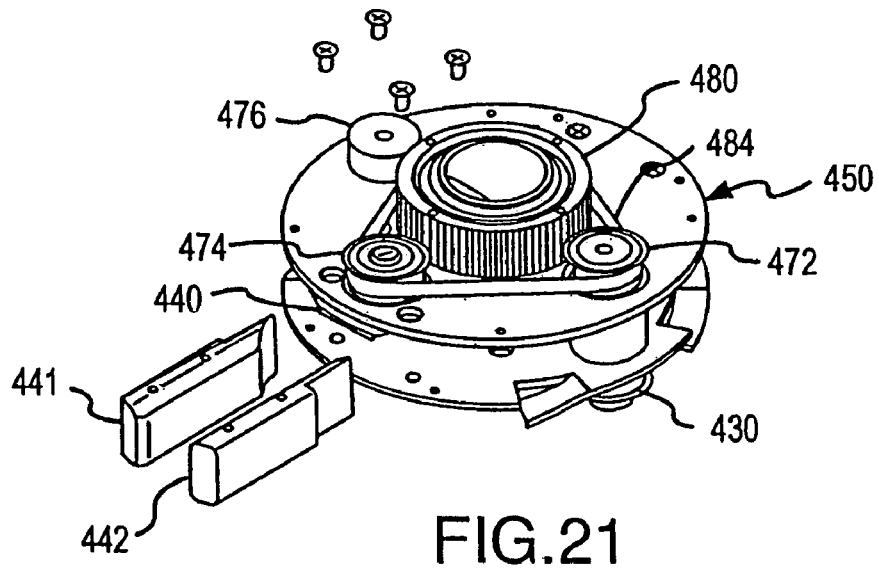
Figure 22:
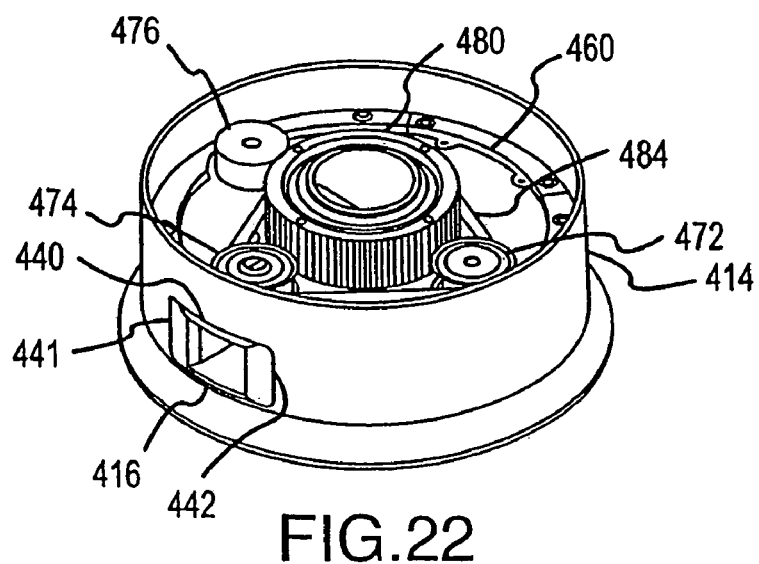

FIGS. 20-22 are provided to further illustrate the assembly of the centrifuge 210 and particularly, the installation and positioning of the skid plate 440. As shown, the upper pulley 480, satellite pulley 472, tensioner 474, spinner 476, and belt 484 have been mounted on the drive core assembly 450 in FIG. 20. The skid plate 440 is shown prior to installation. In FIG. 21, the skid plate 440 is shown installed within the core of the assembly 450 and prior to installation of side plates 441, 442 (note, the curved surfaces for contacting the tubing of the disposable 340 at the bend of the tubing in the core drive assembly 450 and similar curved surfaces are provided on side plates 456, 458 used with the diverter 454). FIG. 22 illustrates a portion of the centrifuge 210 after installation of the side walls 441, 442 and skid plate 440 and defining a tube exit path from the window 416 in the shield 414.

The operation of the operations module 26 in connection with the interface detector 62 has been discussed in some detail with reference to FIG. 2. However, because sensing the RBC-PRP interface with the detector 62 is an important feature of the invention, it may be useful to discuss further a sensing algorithm(s) utilized within the interface detector 62 (which may be a separate module or a part of the control system 12) along with the selective operation of the centrifuge 54 by the control system and operation of the interface detector 62, which includes a light source and return light sensor, in sensing the RBC-PRP interface within the separation chamber 56 (or more specifically, within a chamber 342 positioned within a disposable 340 as shown in FIGS. 8-10).

Generally, the interface sensing algorithm operates differently during four phases of the system 10 operations. The phases occur during pre-filling (pre-calibration); post filling, post RBC separation, and during RBC fast withdrawal (calibration); post filling, post RBC separation, and during RBC fast withdrawal (operation monitoring); and slow withdrawal of RBC (interface detection). During the first phase of pre-calibration, the interface detector 62 detects the presence of a signal based on the transmission of light (e.g., through the light pipes and chamber on the disposable) and sensing of a portion of the light returning to a sensor within the interface detector 62. Typically, positive triggers (i.e., light sensor output signals above a preset level) will occur on a regular basis or period depending on the light source and the configuration of the chamber and centrifuge, e.g., every 30 milliseconds or other period of time. During the second phase or calibration phase, a calibrated trigger level is determined by the sensing algorithm by evaluating signals received when RBC is known to be in the chamber between the two light pipes and blocking the signal and comparing any received signals or noise with the pre-calibration or chamber empty signals. Generally, the calibrated trigger level calculation includes determining a mean and a standard deviation of the signals.

During the third phase or monitoring phase, the interface detector acts to detect the absences of the signal because during normal operations there should be no positive sensor detects (i.e., detection of sensor outputs above the calibrated trigger level) when the RBCs are between the light pipes or in the path between the light source and the light sensor. During the fourth phase or interface detection phase, the interface detector via the detection software or algorithm detects the presence of PRP in the chamber between the light pipes in the disposable (i.e., in the nipple of the chambers). The detection algorithm generally is configured to wait for a set of or number of sensor output signals to be received above the trigger level (i.e., receipt of a set number of trigger signals). In one embodiment, four trigger signals are received prior to the interface detector indicating the presence of the RBC/PRP interface.

The following is a more detailed explanation of one useful technique of operating the system with the interface detector and sensing algorithm or software. Before filling of the chamber begins and while the centrifuge is spinning at the dwell rate (e.g., 1000 RPM), the sensor trigger level is set to 1.0 Volt. After the sensor trigger level is set, the sensing software monitors the sensor detection circuitry in the interface detector. When the chamber is empty, the sensor should trigger positive detections synchronized with the rotation rate of the centrifuge (e.g., at 1000 RPM, for a tested centrifuge and chamber configuration, there was one revolution every 60 milliseconds and because there are two sensor positions every revolution (as can be seen with reference to FIG. 3 and fiber optic assembly 150 and to FIG. 8 and the disposable 214 with level detection assemblies 324, 328), a sensor detect can occur every 30 milliseconds). Since before the chamber is filled the light should go through the chamber walls that are made of clear plastic or other material and through air to the sensor, there should be positive sensor detections every 30 milliseconds before filling. If there are no positive detections prior to filling, then the sensor is not working properly or there is another problem (such as something blocking the light path) and the cycle of operation is terminated. As long as the positive triggers occur every 30 milliseconds as expected, the first phase or pre-calibration and the operating cycle of the centrifuge system is continued.

After filling and RBC separation and during the RBC withdrawal (as indicated by signals from operations module or other device in the control system), the sensing software of the interface detector evaluates the base noise level detected by the light sensor. This is accomplished by calculating a running average and a running standard deviation throughout the RBC withdrawal. This is preferably continuously calculated throughout the fast withdrawal until about one fourth of the fill or initial blood volume has been withdrawn as indicated by monitored operation of the fill pump and signaled by the operations module to the interface detector. During fast RBC withdrawal, the sensor trigger level is set by the sensing software to the calculated mean plus eight (or some other useful multiple) times the standard deviation of the noise level. This results in a calibrated trigger level that has a very low probability of generating false positive detects. Setting the trigger level during RBC fast withdrawal provides a desired level of calibration of the system that is particular to the existing detector, centrifuge, disposable, and chamber configuration.

During RBC fast withdrawal, there should be no positive trigger detects as RBCs are in the chamber and block the light path back to the interface detector. If there are positive detects during this operating phase, the operating cycle of the centrifuge is terminated based on a signal from the interface detector to the operations module. If there are no positive detects, the operating cycle continues until completion of the fast withdrawal. At this point, the interface detector has detected the presence of the signal during pre-calibration or pre-filling and has correctly detected the absence of the signal during RBC fast withdrawal. Hence, any positive detection during later operations such as slow withdrawal is assumed to be based on light making it through the light pipes, the chamber walls, and plasma at a magnitude great enough to trip the light sensor (i.e., at a level above the calibrated trigger level).

During slow withdrawal, the sensor software of the interface detector is used to monitor the sensor for output signals above the trigger level. Positive interface detection by the interface detector requires further that the trigger signals meet the following criteria: (a) the trigger detects are 30 or 60 milliseconds apart (or other repeating time interval depending on the centrifuge configuration) plus or minus a tolerance (such as 5 percent) to allow for variance of the centrifuge rotation rate; (b) more than four or other set number of signals above the trigger level have been detected; and (c) there has not been an unacceptable time gap between any 2 of the received trigger signals, such as a time gap more than 500 to 1000 milliseconds (and if such a gap occurs, a counter is set back to zero for received positive trigger detects). By the time slow RBC withdrawal occurs, the trigger level is set high enough to reduce the risk of noise producing a positive trigger detect. However, the three criteria provided above also act as "secondary" filters that further reduce the risk of false positives caused simply by signal noise.

When the interface detector receives and identifies a required number of positive trigger signals within a required period of time, the interface detector transmits an interface detection signal to the operations module, which responds by topping slow withdrawal and the RBC-PRP interface is now within the sensor assembly light path, i.e., within the chamber between the light paths in the light detection assembly of the disposable. A known and fixed volume of RBC is then withdrawn to clear the chamber and fill line(s) of RBC and allow the withdrawal of plasma. While the specific values of sensor outputs may vary significantly to practice the invention, one tested interface detector, disposable, and chamber arrangement resulted in sensor output with an empty chamber (e.g., during pre-fill) of about 1.8 volts, in sensor output with RBCs in the sensor light path of about 0.480 volts (which represents noise levels detected by the sensor), and in sensor output through plasma (or at an RBC-PRP interface) of between about 1.0 and 1.4 volts.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. For example, embodiments using a 60 cc fill or supply syringe and a withdraw or collection volume of 3 to 10 cc into a 10 cc syringe were discussed in detail to fully explain the functioning of separation and collection systems according to the invention, but those skilled in the art will readily understand that numerous other sizes and volumes of syringes may be used to practice the invention and that a number of the process steps (described with reference to FIG. 2) may be varied to better suit these different volumes. Significantly, the above embodiments of the invention are configured to use low centrifugal forces and lower centrifuge speeds to control plugging of separated RBCs and other components in the separation chamber and its ports. With the separated components not as tightly packed, however, the operations had to better controlled and vibration tightly controlled and these attributes were achieved by the described arrangements and combinations of features and processes that led to reduced vibration of the centrifuge, alignment of components and particularly of the chamber and the interface optics to detect the RBC/PRP interface, and self-balancing of the fluid in the system and of the balancing of the rotating components.

When the disposable 340 is installed on the arm assembly 144 and within the caddy 214 and centrifuge 210, a loop is formed in part due to the skid plate 440 (and tube path 490) and an arc is defined between the window 416 in the shield 410 of the centrifuge 210 and the latch 148 on the arm assembly 144. The loop is unsupported or unrestrained and passes through the center of the centrifuge 210 up to the connector or T 364. When the centrifuge 210 rotates, the loop is forced outward or away from the rotating centrifuge 210 and pulls downward on the tubing runs 366, 360, 362 and, significantly, on the disposable chamber 342. Without this downward force on the chamber 342, the chamber 342 may, in some cases, move slightly within the caddy 214, but the design of the disposable 340 and combined design of the caddy 214, centrifuge 210, and arm assembly 144 provide adequate restraining forces that are useful for aligning the chamber 342 within the caddy 214 and relative to interface sensors.

What is claimed is:

1. An apparatus for processing blood comprising:
   a centrifuge assembly including a centrifuge, a separation container and a drive assembly for rotating the centrifuge about a rotation axis;
   flexible tubing for transferring blood between a first container to the separation container and for transferring a separated fluid from the separation container to a collection container; and
   a loop device for defining a loop in the flexible tubing, the loop device having an arm assembly including a latch for mating with and supporting a tube clamp and an arm for positioning the latch a distance from the centrifuge, the latch being positioned such that the tube clamp is positioned on the rotation axis of the centrifuge.

2. The apparatus of claim 1, wherein the first container is a syringe.

3. The apparatus of claim 1, wherein the second container is a syringe.

4. The apparatus of claim 1, wherein the loop device includes contact surfaces configured for reduced wear of portions of the flexible tubing abutting the contact surfaces.

5. The system of claim 1, wherein the separation container includes two sections separated by a divider element that includes a vent that is in communication with both sections, wherein each section includes a cylindrical elongated portion adjacent the divider element, a collection portion with a side wall that slopes inward toward the central axis of the section to define a reducing circular cross-section along the central axis, a cylindrical nipple attached to the collection portion, and a port fluidly connected to the flexible tubing.

* * * * *

UNITED STATES PATENT AND TRADEMARK OFFICE
CERTIFICATE OF CORRECTION

| | | Page 1 of 1 |
|---|---|---|
| PATENT NO. | : 7,867,159 B2 | |
| APPLICATION NO. | : 11/810071 | |
| DATED | : January 11, 2011 | |
| INVENTOR(S) | : Dolecek et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 317 days.

Signed and Sealed this
Tenth Day of May, 2011

David J. Kappos
*Director of the United States Patent and Trademark Office*